(12) United States Patent
Mauldin et al.

(10) Patent No.: US 11,478,287 B2
(45) Date of Patent: Oct. 25, 2022

(54) FENESTRATED IMPLANT

(71) Applicant: SI-Bone Inc., Santa Clara, CA (US)

(72) Inventors: Richard G. Mauldin, Erie, CO (US);
Scott A. Yerby, Montara, CA (US);
Mark A. Reiley, Delray Beach, CT (US); Bret Schneider, San Jose, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 17/650,473

(22) Filed: Feb. 9, 2022

(65) Prior Publication Data
US 2022/0249146 A1 Aug. 11, 2022

Related U.S. Application Data

(63) Continuation of application No. 16/552,912, filed on Aug. 27, 2019, now Pat. No. 11,291,485, which is a continuation of application No. 13/888,249, filed on May 6, 2013, now Pat. No. 10,426,533.

(60) Provisional application No. 61/642,681, filed on May 4, 2012.

(51) Int. Cl.
| | |
|---|---|
| *A61B 17/84* | (2006.01) |
| *A61B 17/68* | (2006.01) |
| *A61B 17/70* | (2006.01) |
| *A61B 17/16* | (2006.01) |
| *A61F 2/30* | (2006.01) |

(Continued)

(52) U.S. Cl.
CPC .............. *A61B 17/84* (2013.01); *A61B 17/68* (2013.01); *A61B 17/7055* (2013.01); *A61B 17/1604* (2013.01); *A61B 17/1664* (2013.01);
*A61B 17/1671* (2013.01); *A61B 17/1697* (2013.01); *A61B 17/1757* (2013.01); *A61B 17/8897* (2013.01); *A61F 2002/30995* (2013.01)

(58) Field of Classification Search
CPC ... A61B 17/72; A61B 17/744; A61B 17/7208; A61B 17/7283; A61B 17/846; A61B 17/848; A61B 17/7098
See application file for complete search history.

(56) References Cited

U.S. PATENT DOCUMENTS

| | | |
|---|---|---|
| 1,951,278 A | 3/1934 | Ericsson |
| 2,136,471 A | 11/1938 | Schneider |
| 2,243,717 A | 5/1941 | Moreira |

(Continued)

FOREIGN PATENT DOCUMENTS

| | | |
|---|---|---|
| CN | 1128944 A | 8/1996 |
| CN | 1190882 A | 8/1998 |

(Continued)

OTHER PUBLICATIONS

ACUMED; Acutrak Headless Compressioin Screw (product information); 12 pgs; ©2005; retrieved Sep. 25, 2014 from http://www.rcsed.ac.uk/fellows/Ivanrensburg/classification/surgtech/acumed/manuais/acutrak-brochure% 200311.pdf.

(Continued)

*Primary Examiner* — Anu Ramana
(74) *Attorney, Agent, or Firm* — Shay Glenn LLP

(57) ABSTRACT

The present invention relates generally to implants used in medical procedures such as bone fixation or fusion. More specifically, this application relates to fenestrated implants used in bone fixation or fusion.

11 Claims, 33 Drawing Sheets

(51) Int. Cl.
  *A61B 17/17* (2006.01)
  *A61B 17/88* (2006.01)

(56) References Cited

U.S. PATENT DOCUMENTS

| | | |
|---|---|---|
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A * | 10/1995 | Kuslich ............... A61F 2/446 606/907 |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kehrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A * | 4/2000 | Moore ............... A61F 2/30988 606/86 R |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Micheison |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |

(56) References Cited

U.S. PATENT DOCUMENTS

| | | | |
|---|---|---|---|
| 6,669,529 B1 | 12/2003 | Searles |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisetmann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Micheison |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,648,509 B2 | 1/2010 | Stark |
| 7,686,805 B2 | 3/2010 | Micheison |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 * | 12/2010 | Nelson ............... A61B 17/7275 606/62 |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Micheison |
| 8,066,709 B2 | 11/2011 | Micheison |
| 8,092,505 B2 * | 1/2012 | Sommers ............... A61B 17/68 606/317 |
| 8,142,481 B2 | 3/2012 | Warnick |
| 8,202,305 B2 | 6/2012 | Reiley |
| 8,221,499 B2 * | 7/2012 | Lazzara ............... A61L 27/50 433/201.1 |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 * | 9/2014 | Reiley .................. A61B 17/846 606/86 R |
| 8,840,651 B2 | 9/2014 | Reiley |
| 8,845,693 B2 | 9/2014 | Smith et al. |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 * | 6/2015 | Mauldin ............. A61F 2/30988 |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbbing et al. |
| 9,375,243 B1 | 6/2016 | Vestgaarden |
| 9,375,323 B2 | 6/2016 | Reiley |
| 9,445,852 B2 | 9/2016 | Sweeney |
| 9,486,264 B2 | 11/2016 | Reiley et al. |
| 9,492,201 B2 | 11/2016 | Reiley |
| 9,510,872 B2 | 12/2016 | Donner et al. |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| 9,615,856 B2 | 4/2017 | Arnett et al. |
| 9,622,783 B2 | 4/2017 | Reiley et al. |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,820,789 B2 | 11/2017 | Reiley |
| 9,839,448 B2 | 12/2017 | Reckling et al. |
| 9,848,892 B2 | 12/2017 | Biedermann et al. |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 | 5/2018 | Reiley et al. |
| 9,993,276 B2 | 6/2018 | Russell |
| 10,004,547 B2 | 6/2018 | Reiley |
| 10,058,430 B2 | 8/2018 | Donner et al. |
| 10,166,033 B2 | 1/2019 | Reiley et al. |
| 10,194,962 B2 | 2/2019 | Schneider et al. |
| 10,201,427 B2 | 2/2019 | Mauldin et al. |
| 10,219,885 B2 | 3/2019 | Mamo et al. |
| 10,258,380 B2 | 4/2019 | Sinha |
| 10,271,882 B2 | 4/2019 | Biedermann et al. |
| 10,363,140 B2 | 7/2019 | Mauldin et al. |
| 10,426,533 B2 | 10/2019 | Mauldin et al. |
| 10,653,454 B2 | 5/2020 | Frey et al. |
| 10,729,475 B2 | 8/2020 | Childs |
| 10,799,367 B2 | 10/2020 | Vrionis et al. |
| 10,959,758 B2 | 3/2021 | Mesiwala et al. |
| 11,071,573 B2 | 7/2021 | Schneider et al. |
| 11,116,519 B2 | 9/2021 | Sand et al. |
| 11,147,688 B2 | 10/2021 | Reckling et al. |

(56) References Cited

U.S. PATENT DOCUMENTS

| | | |
|---|---|---|
| 11,234,830 B2 | 2/2022 | Mesiwala et al. |
| 11,291,485 B2 | 4/2022 | Mauldin et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1* | 8/2002 | Angelucci .......... A61B 17/7071 623/17.16 |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074990 A1 | 4/2003 | Roth et al. |
| 2003/0078660 A1* | 4/2003 | Clifford ................ A61F 2/4455 623/17.11 |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiiey et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1* | 5/2008 | Branemark ............ A61L 27/50 623/23.57 |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendiik et al. |
| 2008/0255666 A1 | 10/2008 | Fisher et al. |
| 2008/0255667 A1 | 10/2008 | Horton |

(56) References Cited

U.S. PATENT DOCUMENTS

| | | |
|---|---|---|
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grabowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |

(56) References Cited

U.S. PATENT DOCUMENTS

| | | |
|---|---|---|
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0147397 A1 | 5/2015 | Altschuler |
| 2015/0150683 A1 | 6/2015 | Donner et al. |
| 2015/0182268 A1 | 7/2015 | Donner et al. |
| 2015/0216566 A1 | 8/2015 | Mikhail et al. |
| 2015/0238203 A1 | 8/2015 | Asfora |
| 2015/0250513 A1 | 9/2015 | De Lavigne |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0320469 A1 | 11/2015 | Biedermann et al. |
| 2016/0022429 A1 | 1/2016 | Greenhalgh et al. |
| 2016/0095711 A1 | 4/2016 | Castro |
| 2016/0184103 A1 | 6/2016 | Fonte et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0324643 A1 | 11/2016 | Donner et al. |
| 2016/0374727 A1 | 12/2016 | Greenhalgh et al. |
| 2017/0014235 A1 | 1/2017 | Jones et al. |
| 2017/0049488 A1 | 2/2017 | Vestgaarden |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0209155 A1 | 7/2017 | Petersen |
| 2018/0228621 A1 | 8/2018 | Reiley et al. |
| 2019/0133613 A1 | 5/2019 | Reiley et al. |
| 2019/0159901 A1 | 5/2019 | Mauldin et al. |
| 2019/0298528 A1 | 10/2019 | Lindsey et al. |
| 2019/0298542 A1 | 10/2019 | Kloss |
| 2019/0343640 A1 | 11/2019 | Donner et al. |
| 2019/0343641 A1 | 11/2019 | Mauldin et al. |
| 2019/0343653 A1 | 11/2019 | McKay |
| 2020/0008817 A1 | 1/2020 | Reiley et al. |
| 2020/0246158 A1 | 8/2020 | Bergey |
| 2020/0261240 A1 | 8/2020 | Mesiwala et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiiey |
| 2021/0153911 A1 | 5/2021 | Stuart et al. |
| 2021/0169660 A1 | 6/2021 | Reckling et al. |
| 2021/0212734 A1 | 7/2021 | Mesiwala et al. |
| 2022/0031474 A1 | 2/2022 | Reckling et al. |
| 2022/0096098 A1 | 3/2022 | Sand et al. |
| 2022/0117640 A1 | 4/2022 | Schneider et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 249616281 | 10/2018 |
| EP | 3616634 A1 | 3/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO01/17445 A1 | 3/2001 |
| WO | WO02/3 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2013/000071 A1 | 1/2013 |
| WO | WO2013/119907 A1 | 8/2013 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome, J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Mauldin et al.; U.S. Appl. No. 17/649,544 entitled "Fenestrated implant," filed Jan. 31, 2022.

* cited by examiner

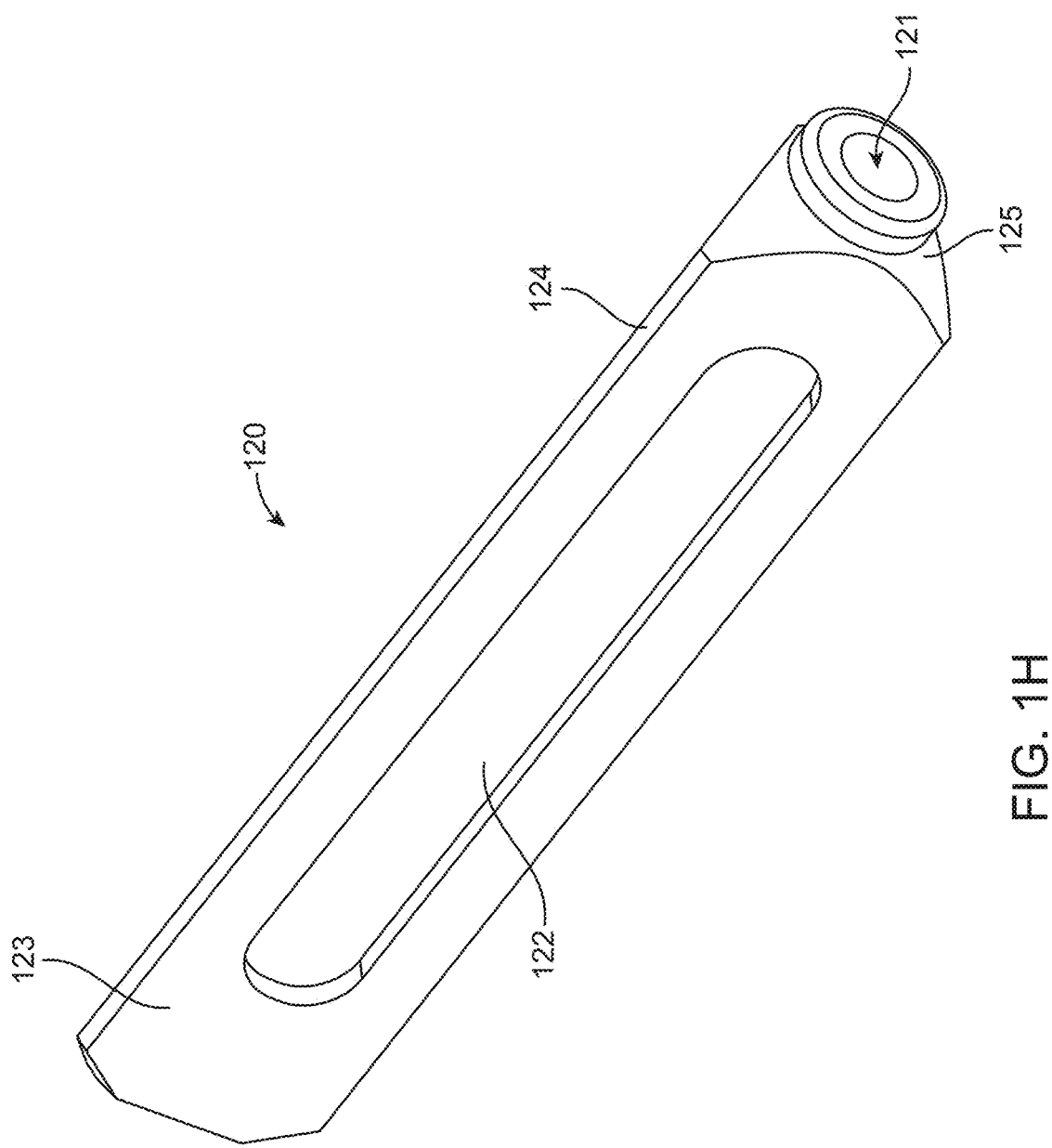

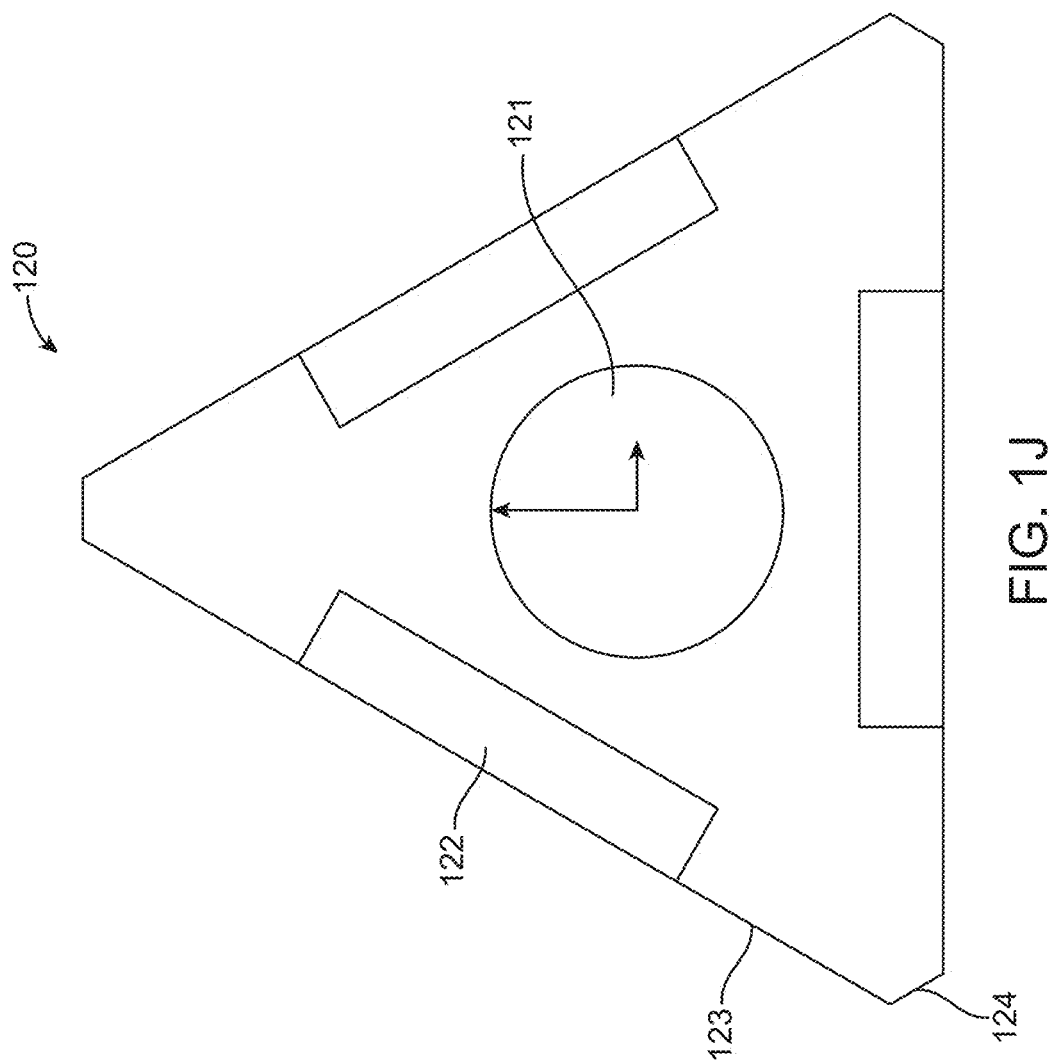

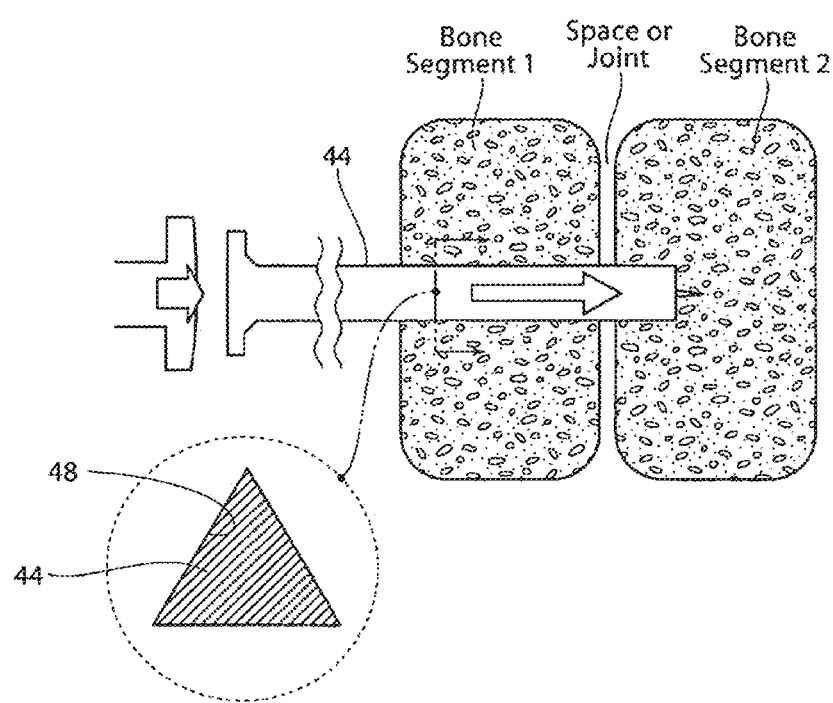

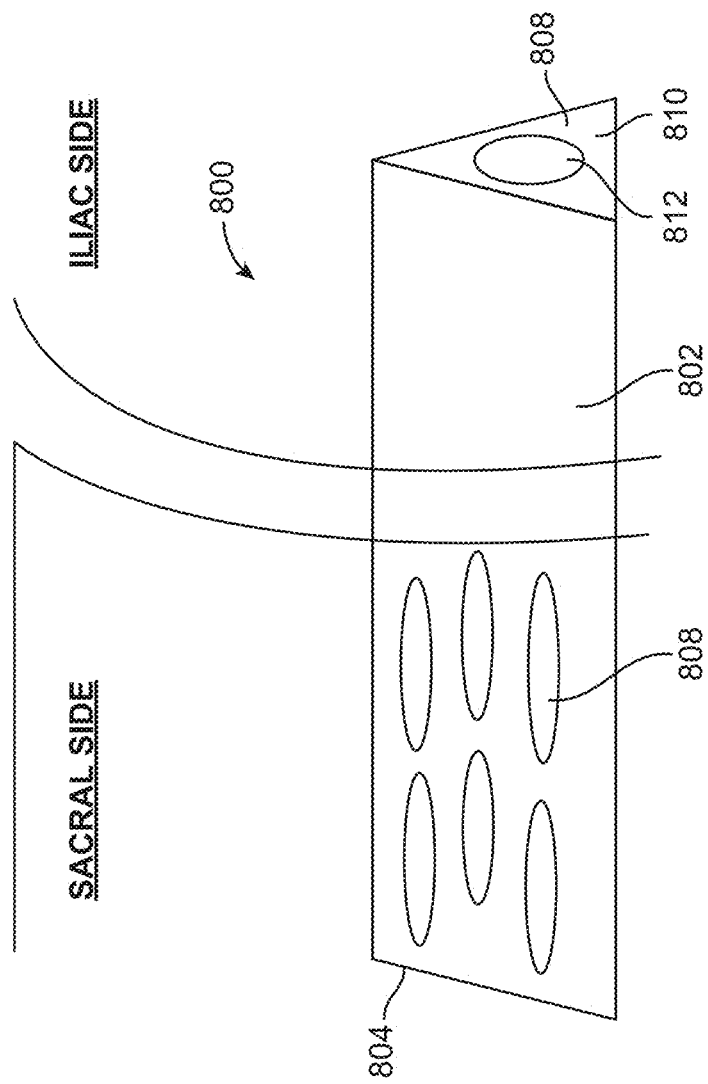

FENESTRATED IMPLANT

CROSS REFERENCE TO RELATED APPLICATIONS

This application is a continuation of U.S. application Ser. No. 16/552,912, filed Aug. 27, 2019, which is a continuation of U.S. application Ser. No. 13/888,249, filed May 6, 2013, now U.S. Pat. No. 10,426,533, which claims the benefit of U.S. Provisional Application No. 61/642,681, filed May 4, 2012, titled "FENESTRATED IMPLANT", each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294 and U.S. Patent Publication No. 2011/0118785.

FIELD

This application relates generally to implants used in medical procedures such as bone fixation or fusion. More specifically, this application relates to fenestrated implants used in bone fixation or fusion.

BACKGROUND

Many types of hardware are available both for the fixation of bones that are fractured and for the fixation of bones that are to be fused (arthrodesed).

For example, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion.

In order to promote bone growth into the implant and enhance fusion of the implant with the bone, pockets or channels can be created in the implant that promote bone growth into the implant. However, these pockets or channels may weaken the structural integrity of the implant, which can also be required to bear large stresses. Therefore, it would be desirable to provide an implant with pockets or channels to promote bone growth while substantially maintaining the structural integrity of the implant.

SUMMARY OF THE DISCLOSURE

The present invention relates generally to implants used in medical procedures such as bone fixation or fusion. More specifically, this application relates to fenestrated implants used in bone fixation or fusion.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, a central lumen extending along the longitudinal axis of the elongate body, and a plurality of holes with openings on the plurality of faces, wherein the holes are in fluid communication with the central lumen.

In some embodiments, the holes are circular. In some embodiments, the holes are oval. In some embodiments, the holes are arranged in a single longitudinal row on each face. In some embodiments, the holes are arranged in a plurality of longitudinal rows on each face.

In some embodiments, the elongate body is coated with a biologic aid.

In some embodiments, the holes have a diameter that is about equal to the diameter of the central lumen. In some embodiments, the holes have a diameter than is between about 0.2 to 0.5 of the width of the faces.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, a central lumen extending along the longitudinal axis of the elongate body, and a plurality of side pockets extending along a portion of each of the plurality of faces, wherein the side pockets have a depth that does not extend to the central lumen.

In some embodiments, each of the plurality of faces has only one side pocket. In some embodiments, each of the side pockets is centered on each of the faces. In some embodiments, the side pockets have a width that is between about 0.2 to 0.8 of the width of the faces and a length that is between about 0.5 to 0.9 of the length of the faces.

In some embodiments, the implant further includes a plurality of holes located within the side pockets, wherein the holes are in fluid communication with the central lumen.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, and a central lumen extending along the longitudinal axis of the elongate body, wherein each one of the plurality of apexes includes a groove that extends along the length of the apex.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, and a central lumen extending along the longitudinal axis of the elongate body, wherein each one of the plurality of apexes includes a plurality of pockets located at discrete points along the length of each apex.

In some embodiments, an implant for bone fixation is provided. The implant can include an elongate body having a longitudinal axis, a distal end, a proximal end, and a rectilinear cross section transverse to the longitudinal axis, a plurality of faces, each face formed from a wall with a thickness between about 2 to 3 mm in thickness, and a plurality of fenestrations disposed on each face.

In some embodiments, the distal end of the elongate body is formed into one or more cutting edges.

In some embodiments, the rectilinear cross section has three sides. In some embodiments, the rectilinear cross section has four sides, such as in FIG. 8C.

In some embodiments, the fenestrations are located on a distal portion of the elongate body that is configured to be implanted within the sacrum of a patient while the proximal portion of the elongate body that is configured to be implanted within the ilium is free from fenestrations.

In some embodiments, the fenestrations are arranged in a staggered pattern.

In some embodiments, the implant further includes a cap on the proximal end of the elongate body, the cap having a hole sized to receive a guide pin.

In some embodiments, the elongate body has an inner surface and an outer surface that are porous. In some embodiments, the elongate body has an inner surface and an outer surface that are roughened. In some embodiments, the elongate body has an inner surface and an outer surface that are plasma coated. In some embodiments, the elongate body has an inner surface and an outer surface that are coated with a biologic aid. In some embodiments, the biologic aid is a bone morphogenetic protein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D are side section views of the formation of a broached bore in bone according to one embodiment of the invention.

FIGS. 5 to 7A and 7B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.

FIGS. 8A, 8B and 8C illustrate embodiments of implant structures with fenestrations.

DETAILED DESCRIPTION

Figure 1A:
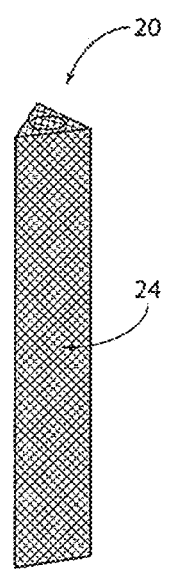
FIGS. 1A-1V illustrate various embodiments of implant structures with different fenestrations.
Figure 3:
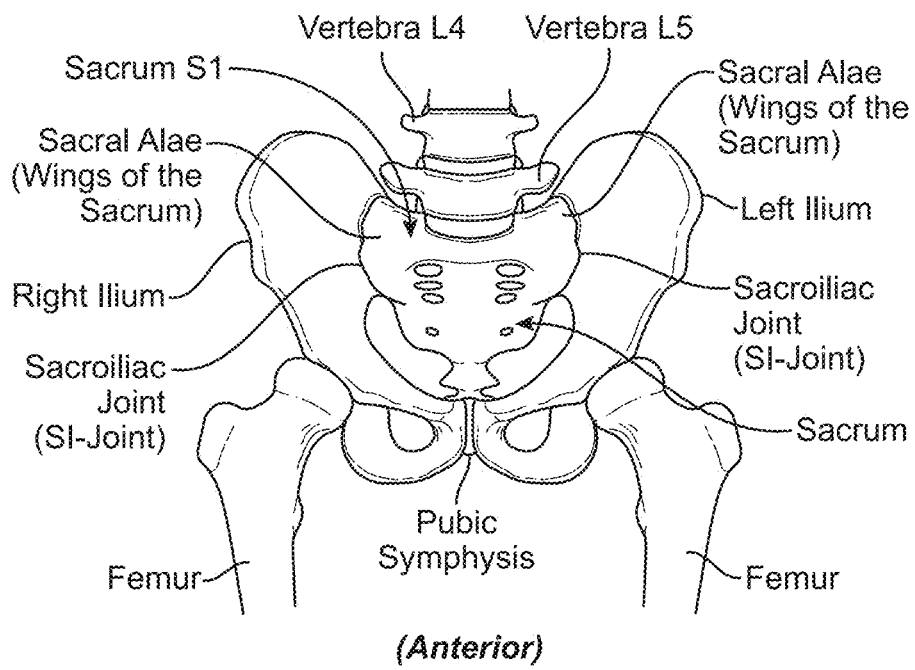
FIGS. 3 and 4 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 4:
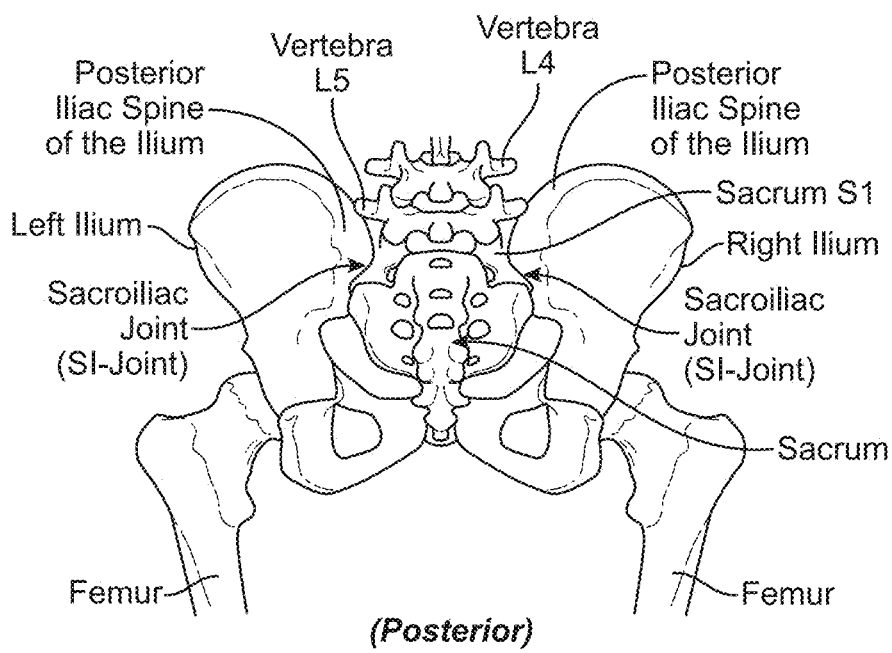

Elongated, stem-like implant structures 20 like that shown in FIG. 1A make possible the fixation of the SI-Joint (shown in anterior and posterior views, respectively, in FIGS. 3 and 4) in a minimally invasive manner. These implant structures 20 can be effectively implanted through the use of a lateral surgical approach. The procedure is desirably aided by conventional lateral and/or anterior-posterior (A-P) visualization techniques, e.g., using X-ray image intensifiers such as a C-arms or fluoroscopes to produce a live image feed that is displayed on a TV screen.

In some embodiments, the implant structures 20 can include pockets, pathways, cavities, openings, fenestrations, channels and/or recesses that allow bone graft materials to be incorporated into the implant structure. These bone graft materials can promote bone growth into and/or around the implant structure, which can reduce the time it takes for the implant structure to be stably integrated with the bone. Bone graft materials can be applied to and/or injected into the implant structure before implantation or applied after implantation by injection of the bone graft material into a proximal cannula or other conduit. In some embodiments, the surfaces of the implant structure 20 can be roughened or textured to promote bone growth and adherence of the bone graft materials. The internal and/or external surfaces can be roughened or textured by mechanical means or can be spray coated with a roughening material.

The bone graft materials can be a liquid, gel, slurry, paste, powder or other form, and can include a biologic aid that can promote and/or enhance bony ingrowth, tissue repair, and/or reduce inflammation, infection and pain. For example, the biologic aid can include growth factors, such as bone morphogenetic proteins (BMPs), hydroxyapatite in, for example, a liquid or slurry carrier, demineralized bone, morselized autograft or allograft bone, medications to reduce inflammation, infection or pain such as analgesics, antibiotics and steroids. In some embodiments, the growth factors can be human recombinant growth factors, such as hr-BMP-2 and/or hr-BMP-7, or any other human recombinant form of BMP, for example. The carrier for the biologic aid can be a liquid or gel such as saline or a collagen gel, for example. The biologic aid can also be encapsulated or incorporated in a controlled released formulation so that the biologic aid is released to the patient at the implant site over a longer duration. For example, the controlled release formulation can be configured to release the biologic aid over the course of days or weeks or months, and can be configured to release the biologic aid over the estimated time it would take for the implant site to heal. The amount of biologic aid delivered to the implant structure can be controlled using a variety of techniques, such as controlling or varying the amount of coating material applied to the implant and/or controlling or varying the amount of biologic aid incorporated into the coating material. In some embodiments, in may be important to control the amount of biologic aid delivered because excessive use of certain biologic aids can result in negative effects such as radicular pain, for example.

In general, any pockets, pathways, cavities, openings, fenestrations, channels and/or recesses in the implant structure may weaken its structural strength, including for example the bending and shear strengths. The following examples of implant structures are variations of the solid triangular implant structure 20 of FIG. 1A, which has a single central, longitudinally oriented lumen or cannula for receiving a guide wire or guide pin. The relative bending and shear strengths can be compared to the cannulated but otherwise solid implant structure 20 of FIG. 1A, which can be assigned a bending strength of 1.00 and a shear strength of 1.00. The relative bending and shear strengths can be modified or optimized for structural strength and ability to promote bone grafting by varying the size, number, spacing, location, orientation, and shape of the pockets, pathways, cavities, openings, fenestrations, channels and/or recesses. Although the embodiments illustrated herein show triangular implant structures, implant structures with different rectilinear shapes, such as rectangular or square, can be used or substituted for the triangular implant structures.

Figure 1B:
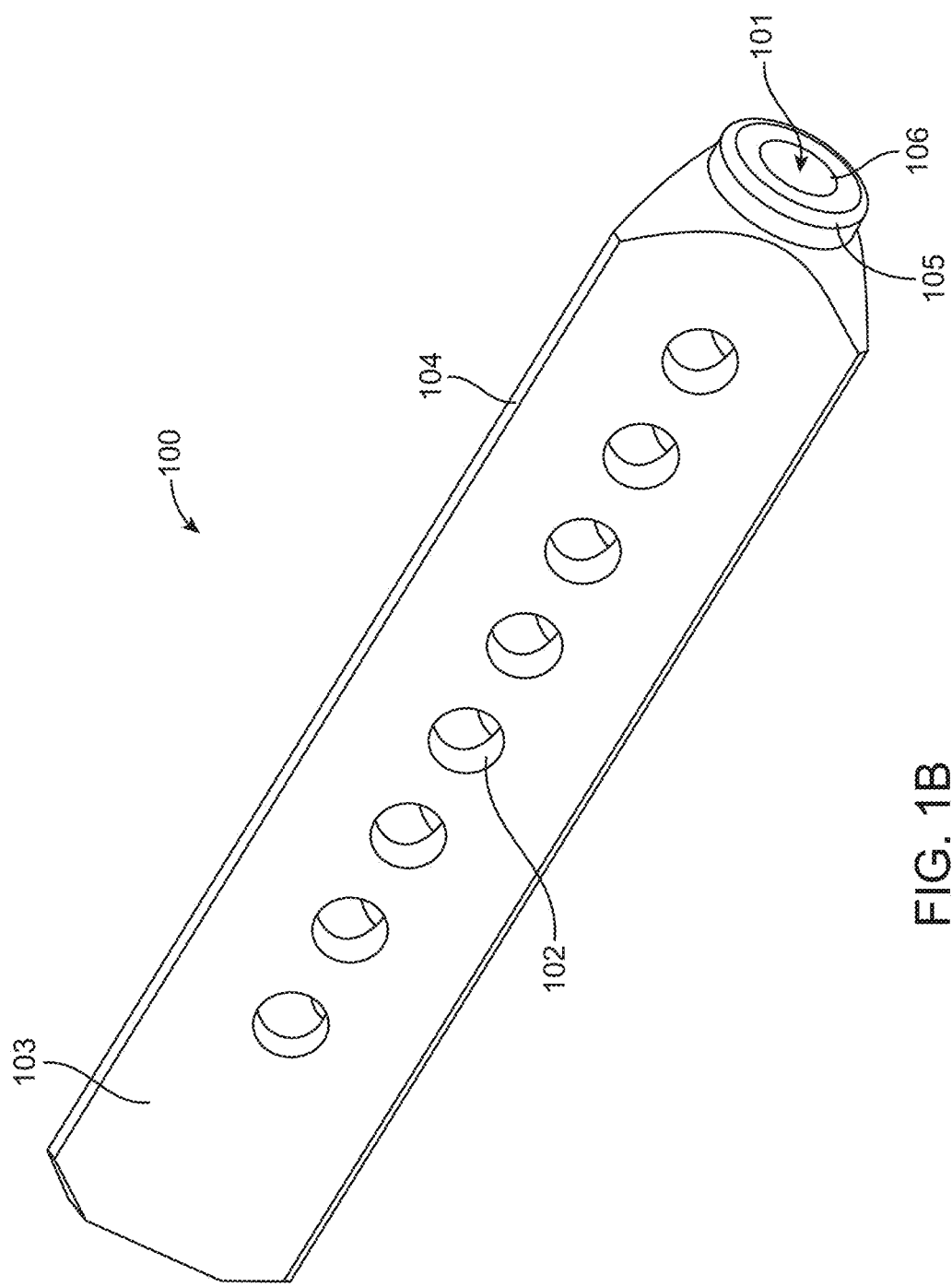
Figure 1C:
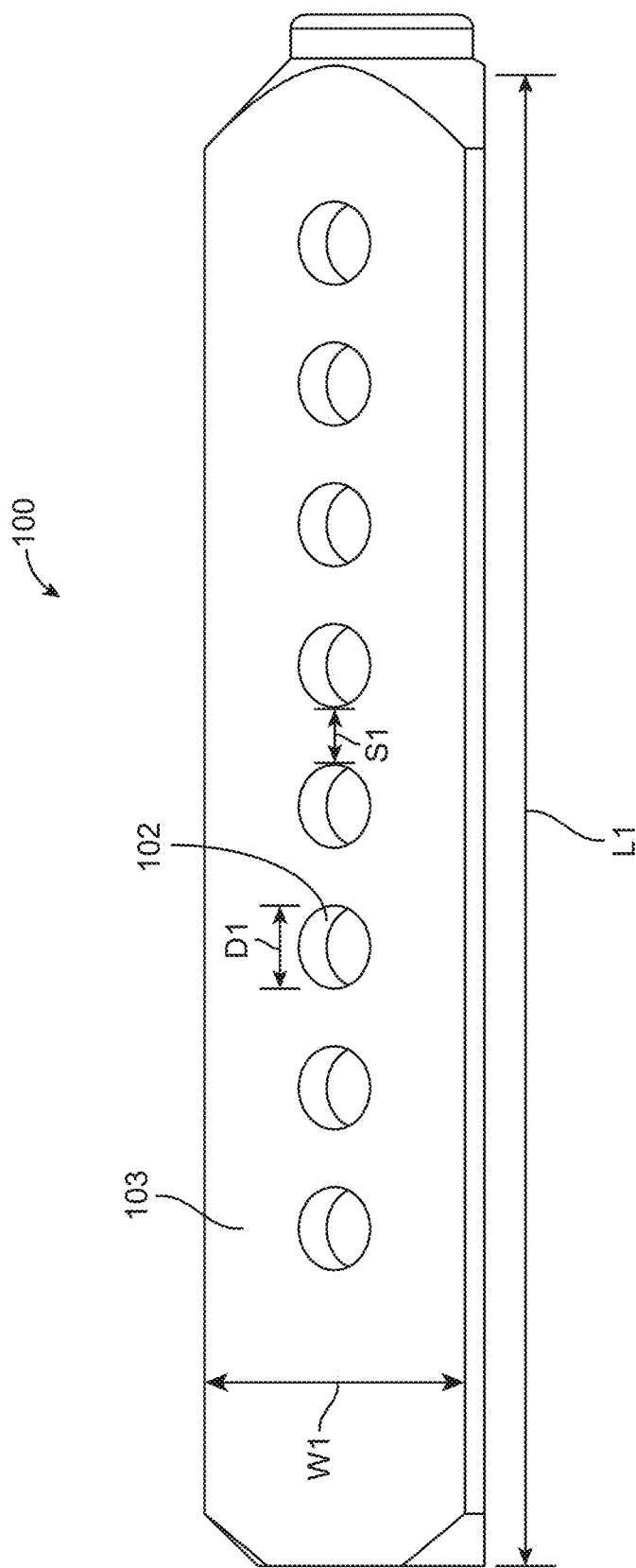
Figure 1D:
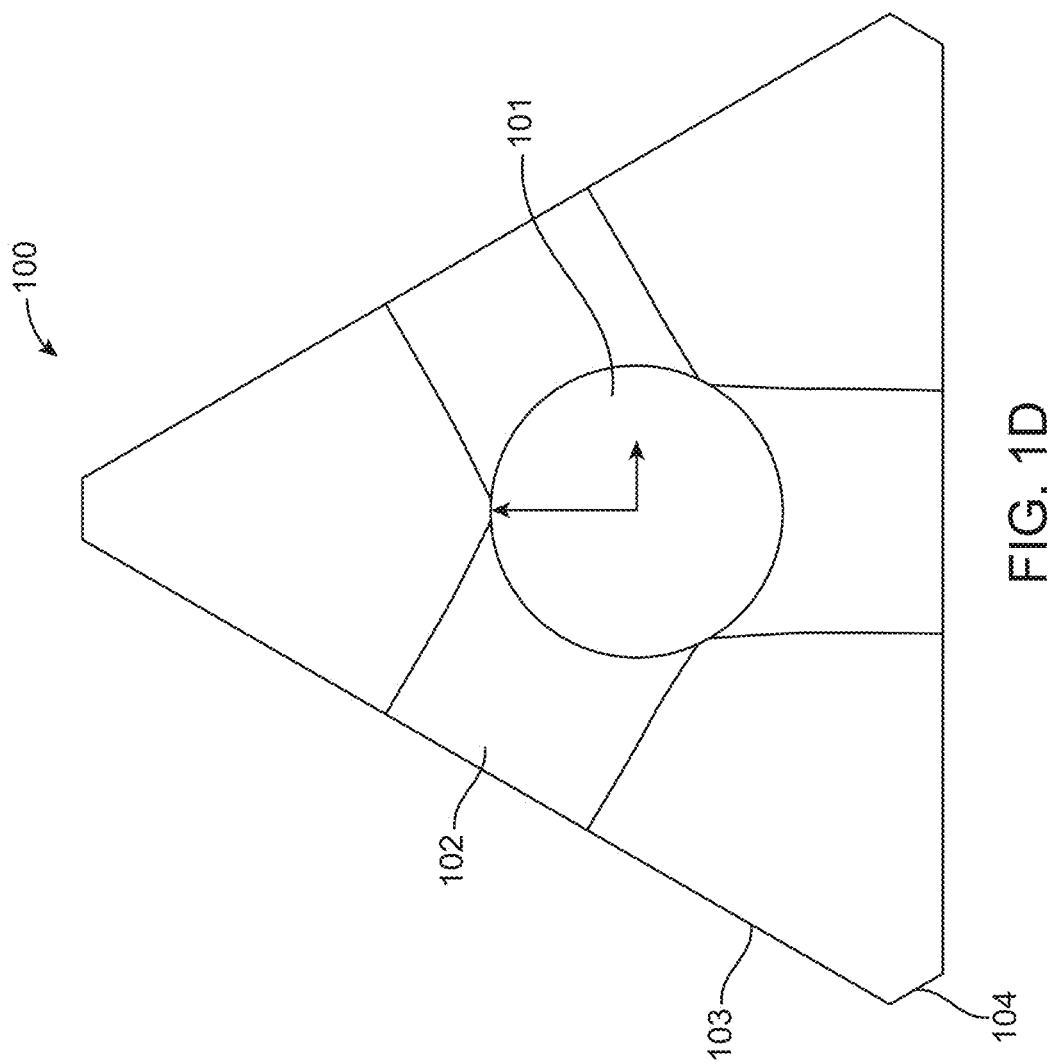

FIGS. 1B-D illustrate an embodiment of a triangular implant structure 100 having a central lumen 101 and a series of holes 102 on each face 103 of the implant structure 100 that reach and provide access to the central lumen 101. The holes 102 can be centered on the face 103 and extend inwardly at an angle that is substantially perpendicular or normal to the face 103 of the implant structure 100. In some embodiments, each apex 104 can be beveled or rounded. In some embodiments, the distal end 105 of the implant structure 100 can be tapered to facilitate implantation into the bone. In some embodiments, the diameter of the holes 102 can be equal to or substantially equal to the diameter of the central lumen 101. In other embodiments, the diameter of the holes 102 can be greater than or less than the diameter of the central lumen 101. In some embodiments, the implant structure 100 illustrated in FIGS. 1B-D has a relative bending strength of about 0.82 and a relative shear strength of about 0.66. In some embodiments, to inject or load the implant structure 100 with bone graft materials, the distal hole 106 of the central lumen 101 can be blocked or sealed so that flow of the bone graft materials fills the central lumen 101 and exits the side holes 102.

In some embodiments, the holes 102 can have a diameter (D1) that is about 0.3 of width (W1) of the face 103 of the implant structure 100. In some embodiments, the holes 102 can have a diameter that is greater than about 0.3 of the width of the face 103 of the implant structure 100. In some embodiments, the holes 102 can have a diameter that is less than about 0.3 of the width of the face 103 of the implant structure 100. In some embodiments, the holes 102 can have a diameter that is between about 0.2 to about 0.5 of the width of the face 103 of the implant structure. In some embodiments, the holes 102 can be separated from adjacent holes 102 by about ⅔ of the hole diameter, where separation distance (S1) is measured by the distance between the circumference of the holes 102. In some embodiments, the holes 102 can be separated from adjacent holes 102 by less than about ⅔ of the hole diameter. In some embodiments, the holes 102 can be separated from adjacent holes 102 by greater than about ⅔ of the hole diameter. In some embodiments, the holes 102 can be separated from adjacent holes 102 by about 0.5 to about 2 times, or about 0.5 to about 1 times the hole 102 diameter. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1E:
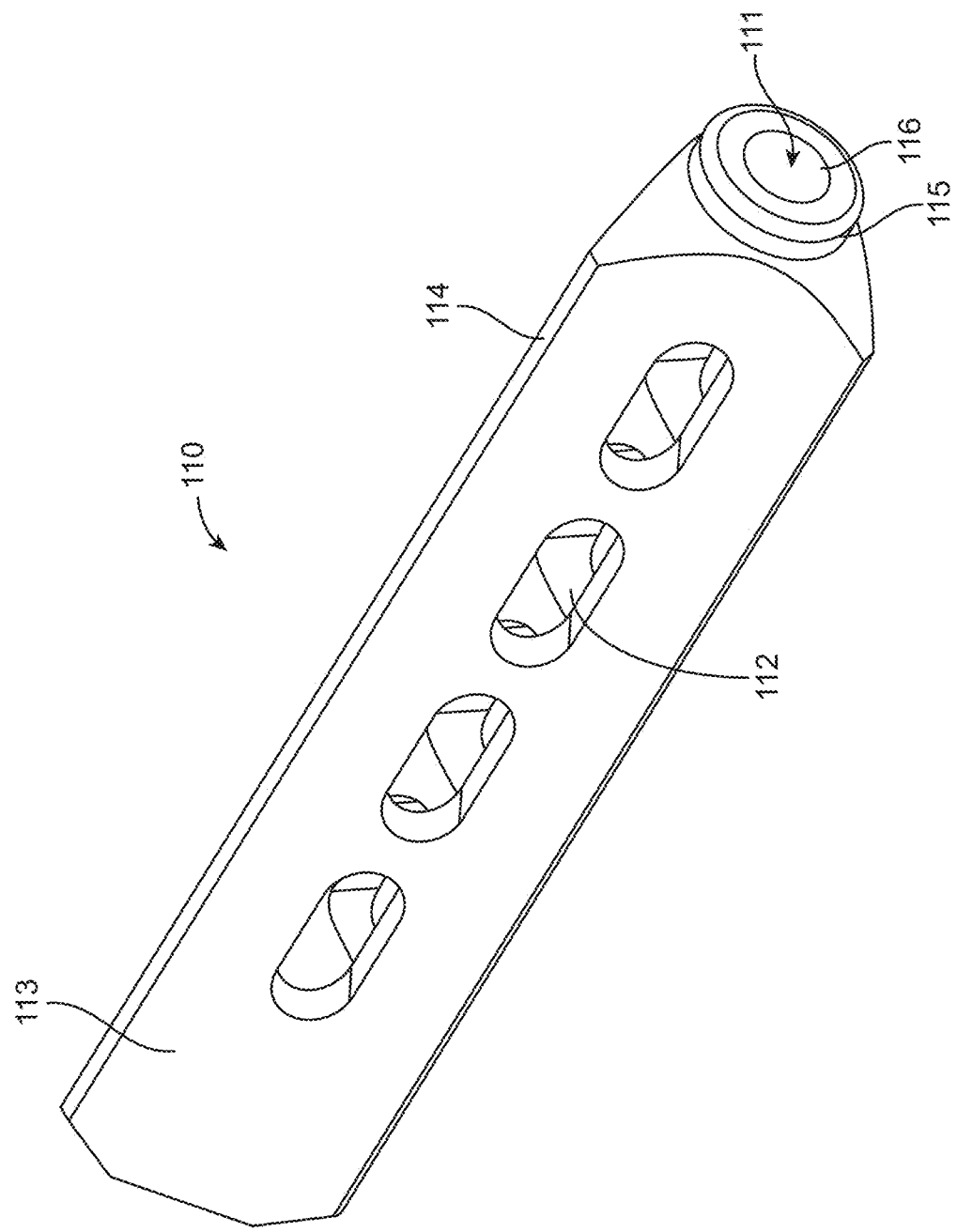
Figure 1F:
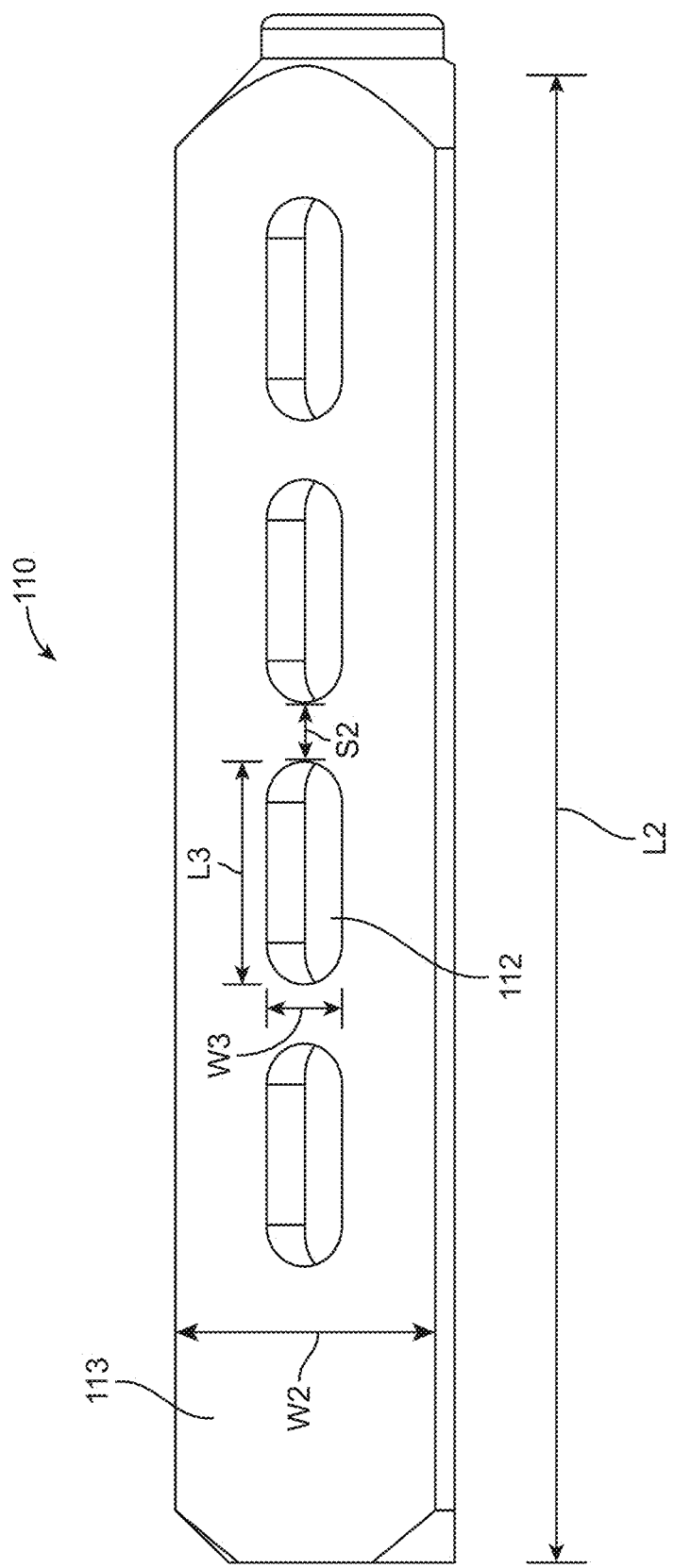
Figure 1G:
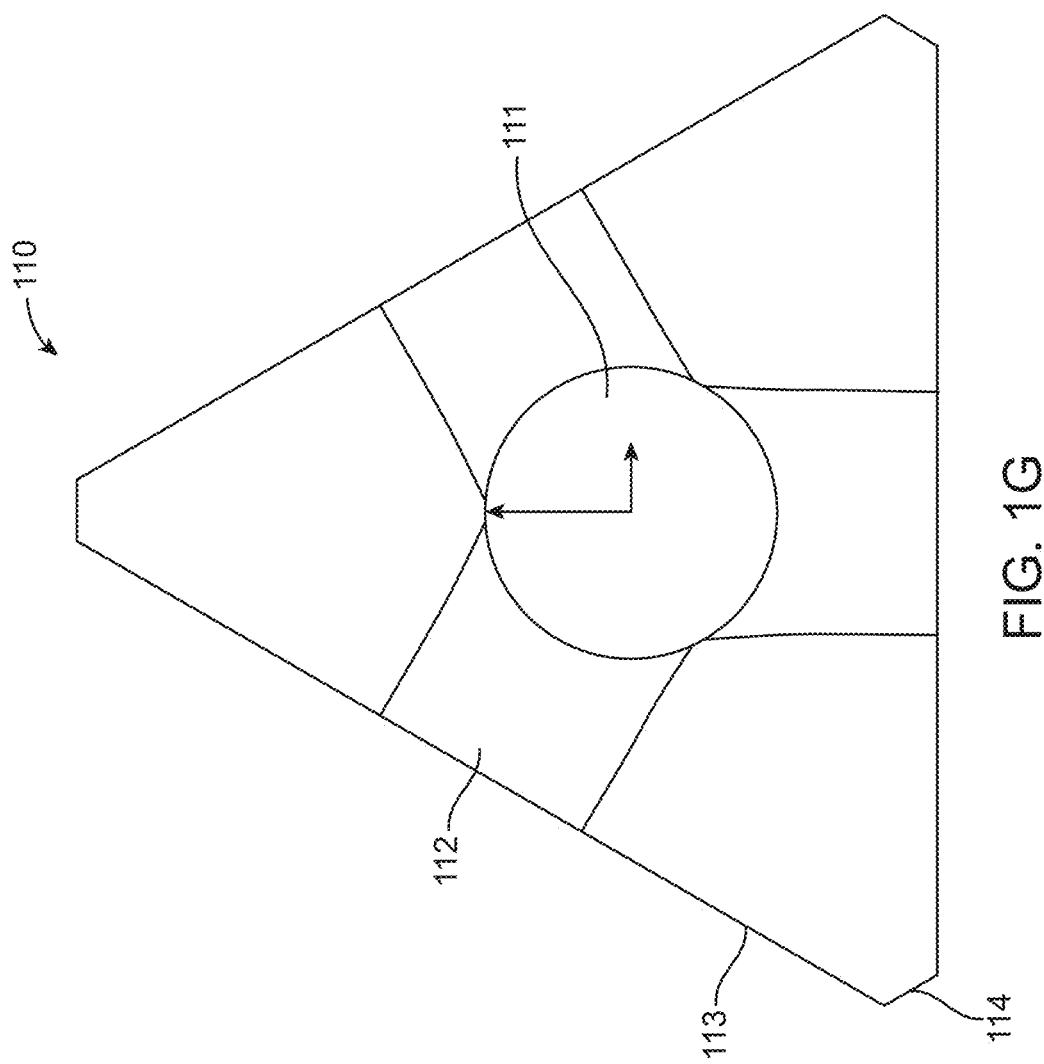

FIGS. 1E-G illustrate another embodiment of an implant structure 110 having a central lumen 111 and a series of slots 112 on each face 113 of the implant structure 110 that reach and provide access to the central lumen 111. The slots 112 can be centered on the face 113 and extend inwardly at an angle that is substantially perpendicular or normal to the face 113 of the implant structure 110. In some embodiments, each apex 114 can be beveled or rounded. In some embodiments, the distal end 115 of the implant structure 110 can be tapered to facilitate implantation into the bone. In some embodiments, the width of the slots can be equal to or substantially equal to the diameter of the central lumen 111. In other embodiments, the width of the slots can be greater than or less than the diameter of the central lumen 111. In some embodiments, the implant structure 110 illustrated in FIGS. 1E-G has a relative bending strength of about 0.82 and a relative shear strength of about 0.66. In some embodiments, to inject or load the implant structure 110 with bone graft materials, the distal hole 116 of the central lumen 111 can be blocked or sealed so that flow of the bone graft materials fills and exits the slots 112.

In some embodiments, the slots 112 can have a width (W3) that is about 0.3 of width (W2) of the face 113 of the implant structure 110. In some embodiments, the slots 112 can have a width that is greater than about 0.3 of the width of the face 113 of the implant structure 110. In some embodiments, the slots 112 can have a width that is less than about 0.3 of the width of the face 113 of the implant structure 110. In some embodiments, the slots 112 can have a width that is between about 0.2 to about 0.6 of the width of the face 113 of the implant structure 110. In some embodiments, the slots 112 can have a length (L3) that is about 0.15 the length (L2) of the face 113. In some embodiments, the slots 112 can have a length that is less than about 0.15 the length of the face 113. In some embodiments, the slots 112 can have a length that is greater than about 0.15 the length of the face 113. In some embodiments, the slots 112 can have a length that is between about 0.1 to 0.4, or about 0.1 to 0.25 the length of the face 113. In some embodiments, the slots 112 are separated (S2) from adjacent slots 112 by about ⅔ width of the slot 112. In some embodiments, the slots 112 are separated from adjacent slots 112 by greater than about ⅔ the width of the slot 112. In some embodiments, the slots 112 are separated from adjacent slots 112 by less than about ⅔ the width of the slot 112. In some embodiments, the slots 112 can be separated from adjacent slots 112 by about 0.5 to about 2 times, or about 0.5 to about 1 times the slot 112 width. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1I:
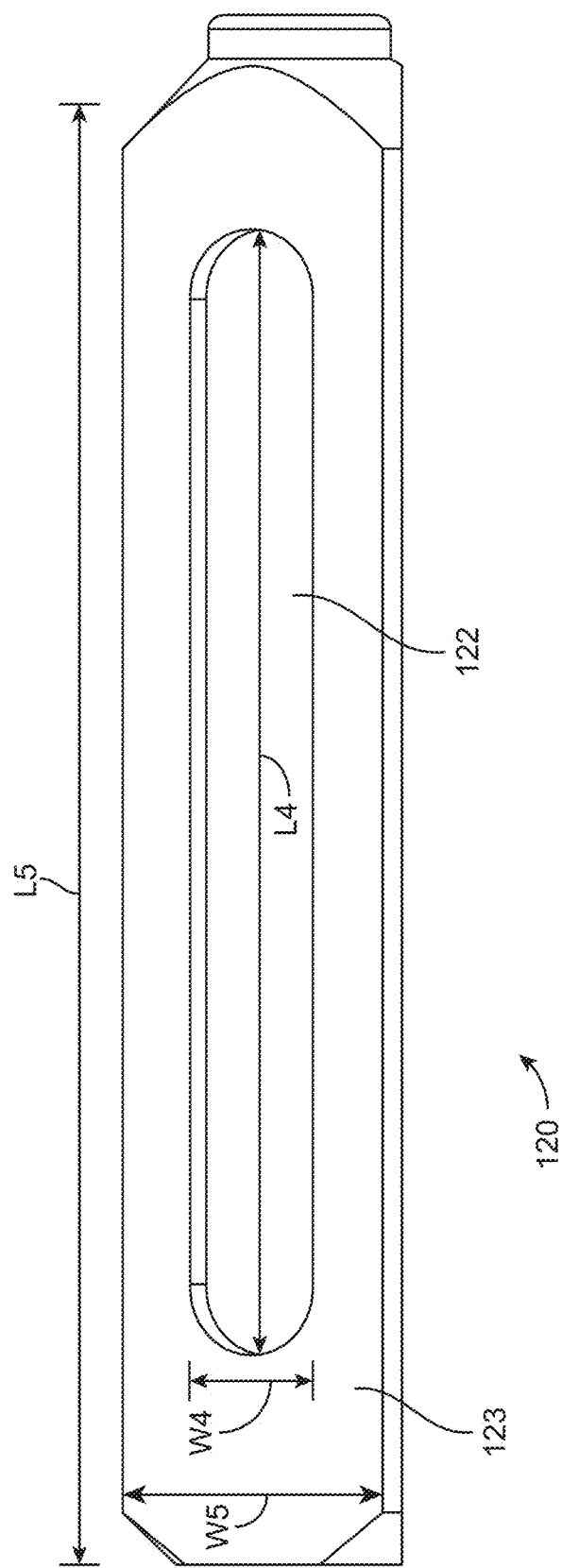

FIGS. 1H-J illustrate another embodiment of an implant structure 120 having a central lumen 121 and a side pocket 122 on each face 123 of the implant structure 120. The side pocket 122 can be a depression, cavity, groove or slot centered on the face 123 having a width, length and depth. In some embodiments, the side pocket 122 is relatively shallow so that it does not extend to the central lumen 121. In some embodiments, each apex 124 can be beveled or rounded. In some embodiments, the distal end 125 of the implant structure 120 can be tapered to facilitate implantation into the bone. In some embodiments, the implant structure 120 illustrated in FIGS. 1H-J has a relative bending strength of about 0.77 and a relative shear strength of about 0.72. In some embodiments, to load the implant structure 120 with bone graft materials, the bone graft material is applied to the side pockets 122 before implantation. In other embodiments, the bone graft material is applied during implantation, as further described in U.S. Patent Application 61/609,043 titled Tissue Dilator and Protector, which is hereby incorporated by reference in its entirety and can be applied to the other implants.

In some embodiments, the side pocket 122 can have a width (W4) that is about 0.5 of width (W5) of the face 123 of the implant structure 120. In some embodiments, the side pocket 122 can have a width that is greater than about 0.5 of the width of the face 123 of the implant structure 120. In some embodiments, the side pocket 122 can have a width that is less than about 0.5 of the width of the face 123 of the implant structure 120. In some embodiments, the side pocket 122 can have a width that is between about 0.2 to about 0.8 of the width of the face 123 of the implant structure 120. In some embodiments, the side pocket 122 can have a length (L4) that is about 0.75 the length (L5) of the face 123. In some embodiments, the side pocket 122 can have a length that is less than about 0.75 the length of the face 123. In some embodiments, the side pocket 122 can have a length that is greater than about 0.75 the length of the face 123. In some embodiments, the side pocket 122 can have a length that is between about 0.5 to 0.9 of the length of the face 123. In some embodiments, the side pocket 122 can have a depth between about 0.2 mm and 5 mm, or between about 0.2 mm and 2 mm, or between about 0.2 and 1 mm. In some embodiments, the side pocket 122 can have a depth between about 0.25 mm, 0.5 mm, 0.75 mm, 1 mm or 2 mm. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1K:
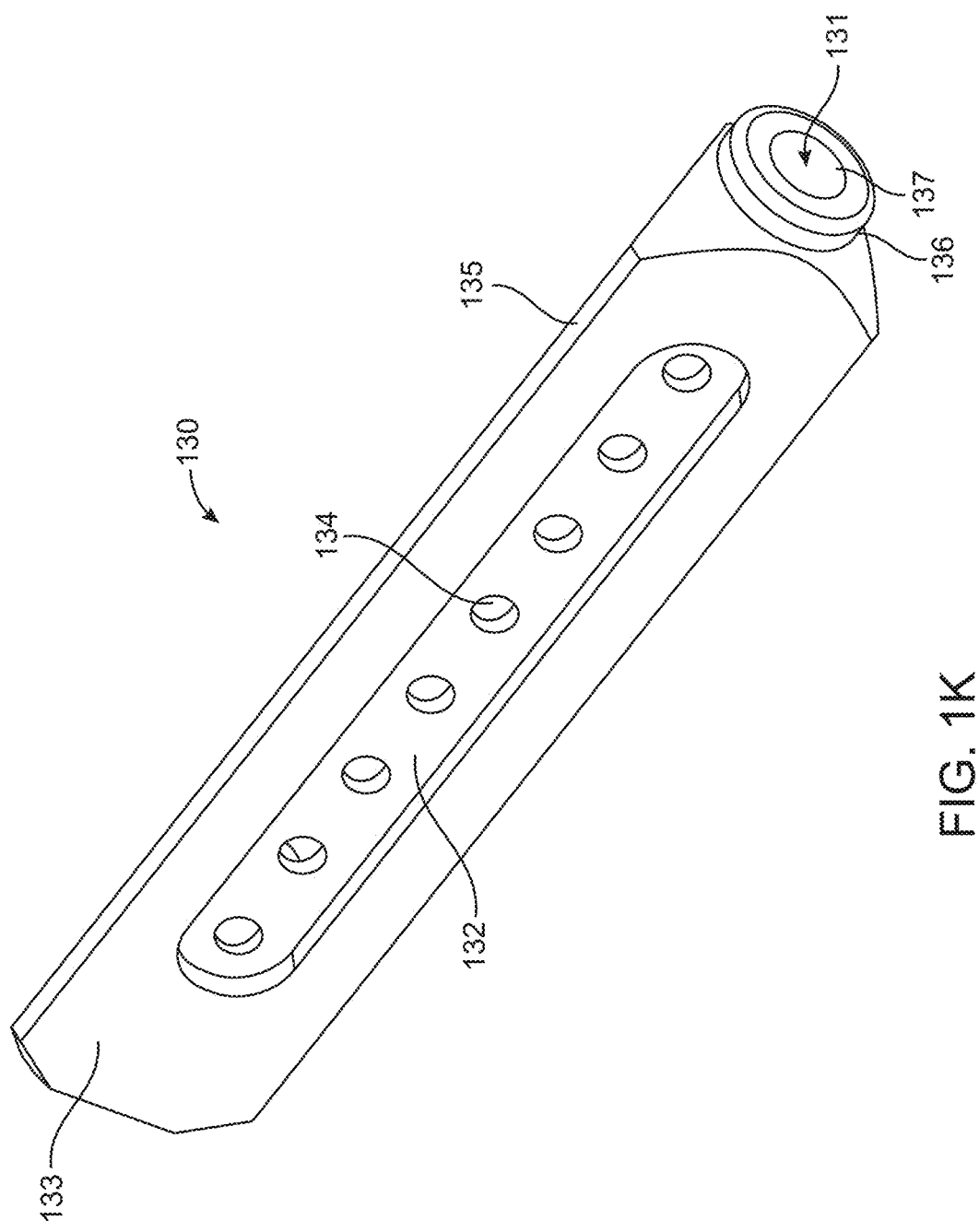
Figure 1L:
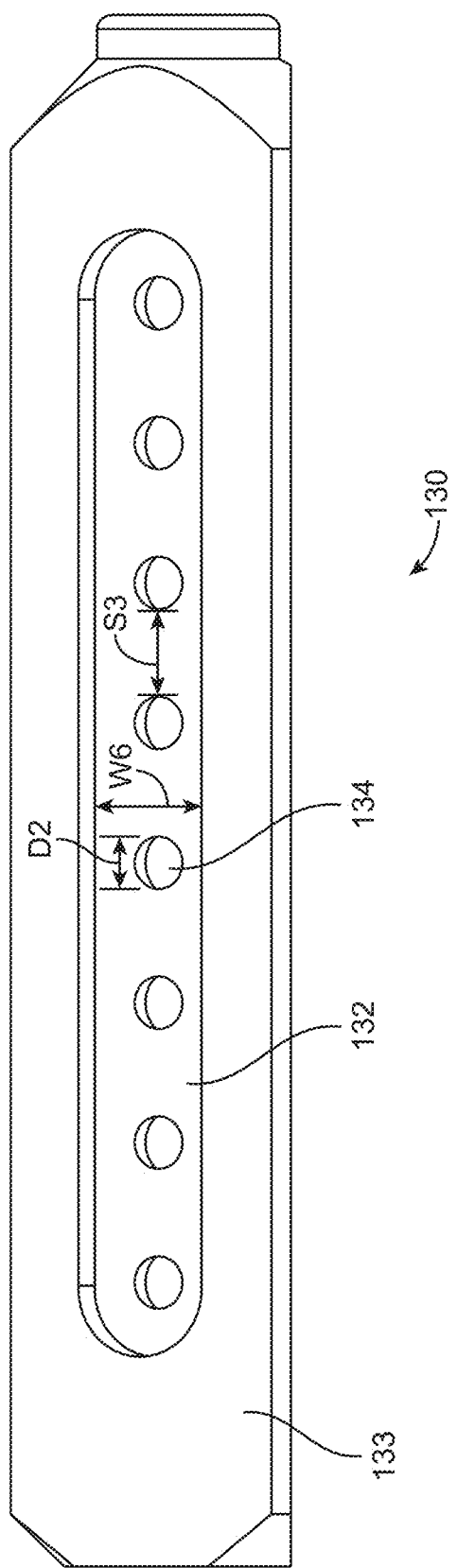
Figure 1M:
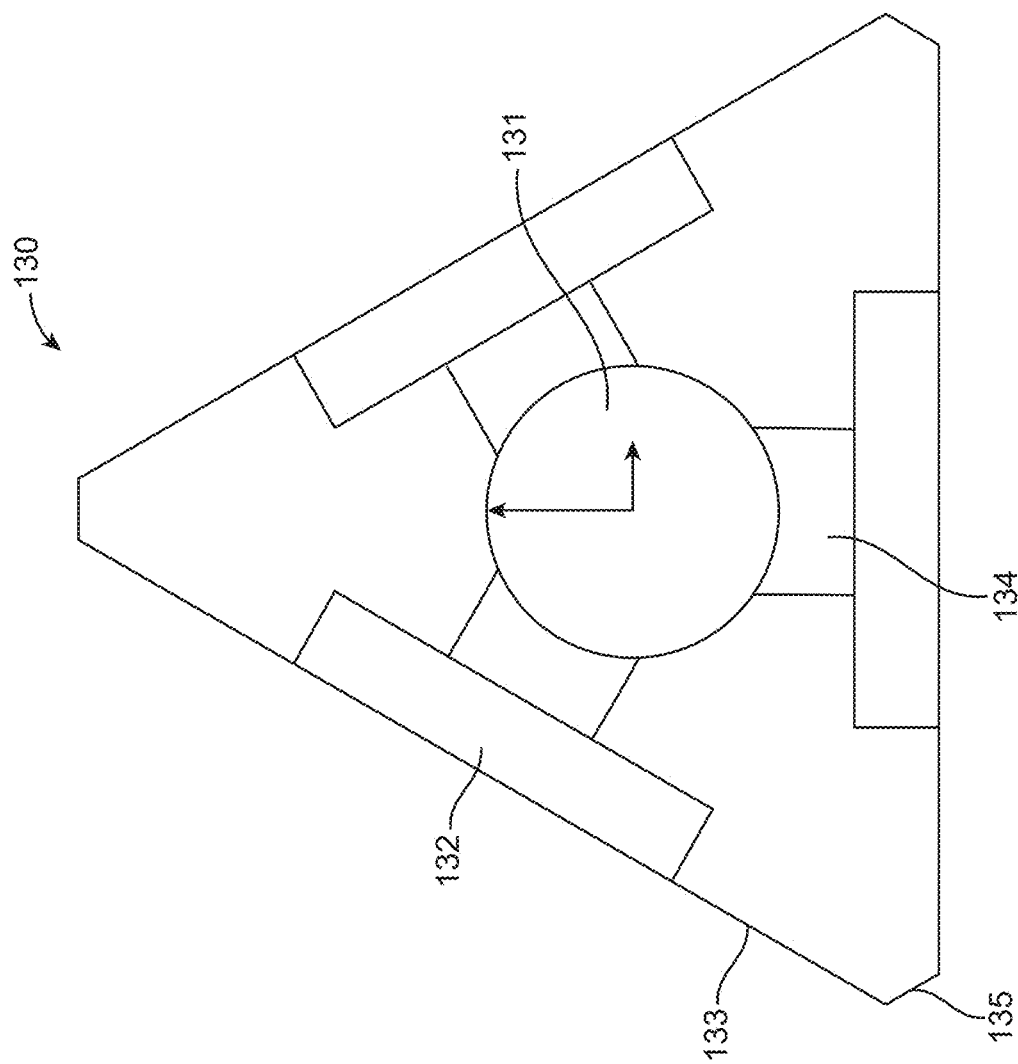

FIGS. 1K-M illustrate another embodiment of an implant structure 130 having a central lumen 131, a side pocket 132 on each face 133 of the implant structure 130, and a plurality of holes 134 located within the side pocket 132. The side pocket 132 in the embodiment illustrated in FIGS. 1K-M can be the same as or be similar to the side pocket 122 previously described above and illustrated in FIGS. 1H-J. Likewise, the holes 134 illustrated in FIGS. 1K-M can be the same as or be similar to the holes 102 previously described above and illustrated in FIGS. 1B-D. In some embodiments, as illustrated in FIGS. 1K-M, the holes 134 have a diameter that is less than the diameter of the central lumen 131. In other embodiments, the holes 134 have a diameter than is equal to or greater than the diameter of the central lumen 131. In some embodiments, each apex 135 can be beveled or rounded. In some embodiments, the distal end 136 of the implant structure 130 can be tapered to facilitate implantation into the bone. In some embodiments, the implant structure 130 illustrated in FIGS. 1K-M has a relative bending strength of about 0.74 and a relative shear strength of about 0.62. In some embodiments, to load the implant structure 130 with bone graft materials, the bone graft material is injected and/or applied to the side pockets 132 and holes 134 before implantation. In other embodiments, the bone graft materials can be injected into the central lumen 131, which can have a distal opening 137 that is blocked off or plugged so that the bone graft materials fill the central lumen 131 and exit out the holes 134 which are in fluid communication with the central lumen 131. As the bone graft materials exit the holes 134, the bone graft material can coat and fill both the holes 134 and the side pocket 132. This injection process can be done before implantation, during implantation, or after implantation.

In some embodiments, the side pocket 132 shown in FIGS. 1K-M has the same or similar dimensions as the side pocket 122 shown in FIGS. 1H-J and described above. In some embodiments, the holes 134 can have a diameter (D2) that is about 0.4 of the width (W6) of the side pocket 132. In some embodiments, the holes 134 can have a diameter that is greater than or less than about 0.4 times the width of the side pocket 132. In some embodiments, the holes 134 can be separated (S3) by about 1.5 times the diameter of the holes 134. In some embodiments, the holes 134 can be separated by greater than or less than about 1.5 times the diameter of the holes 134. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1N:
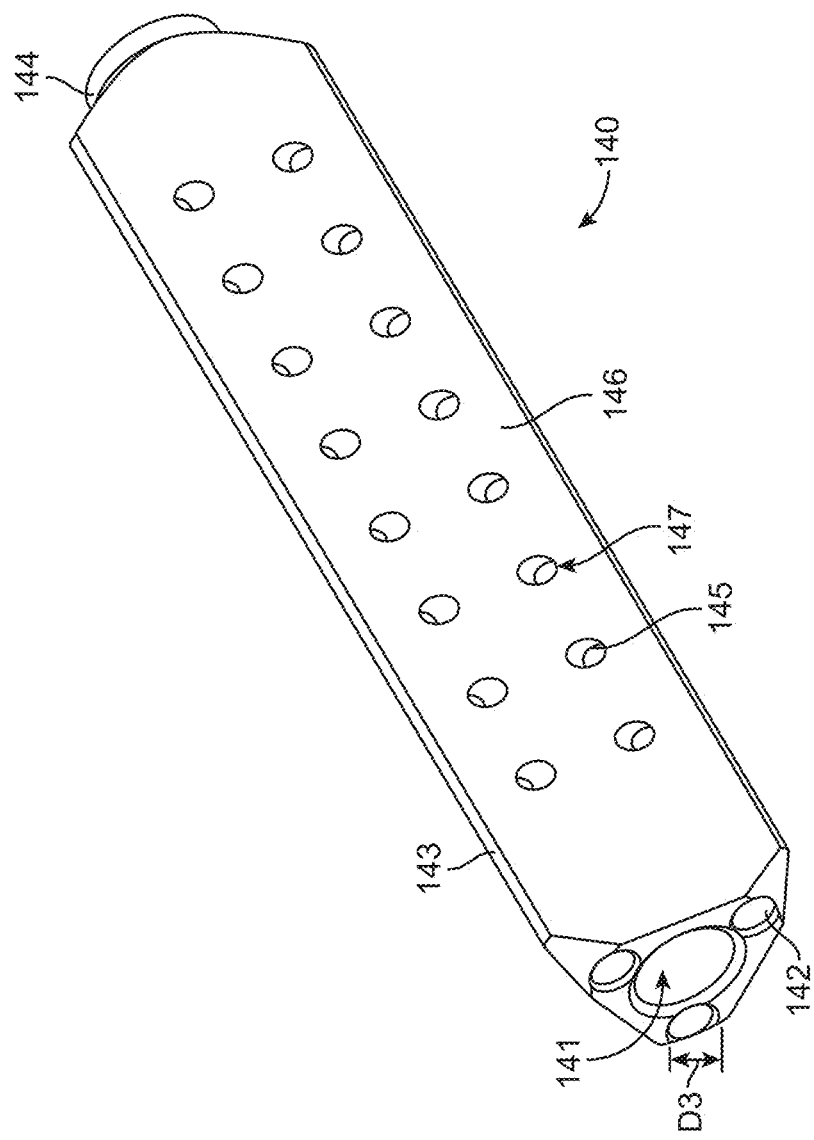
Figure 10:
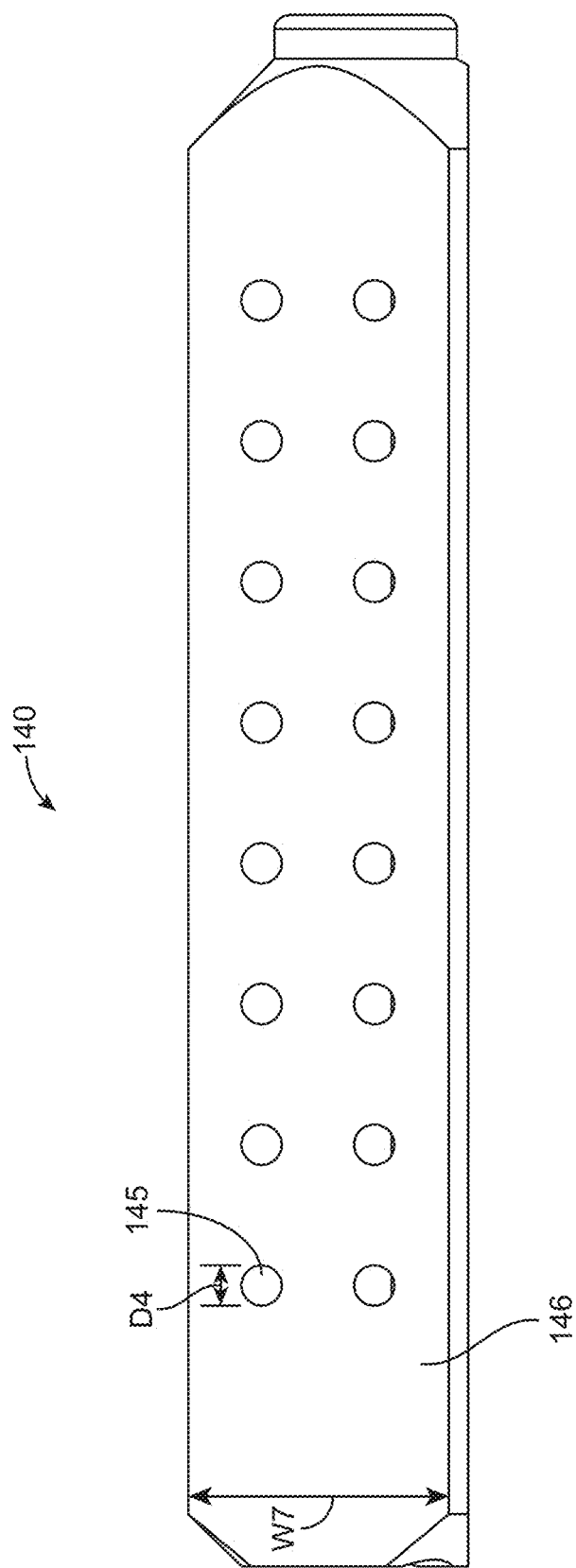
Figure 1P:
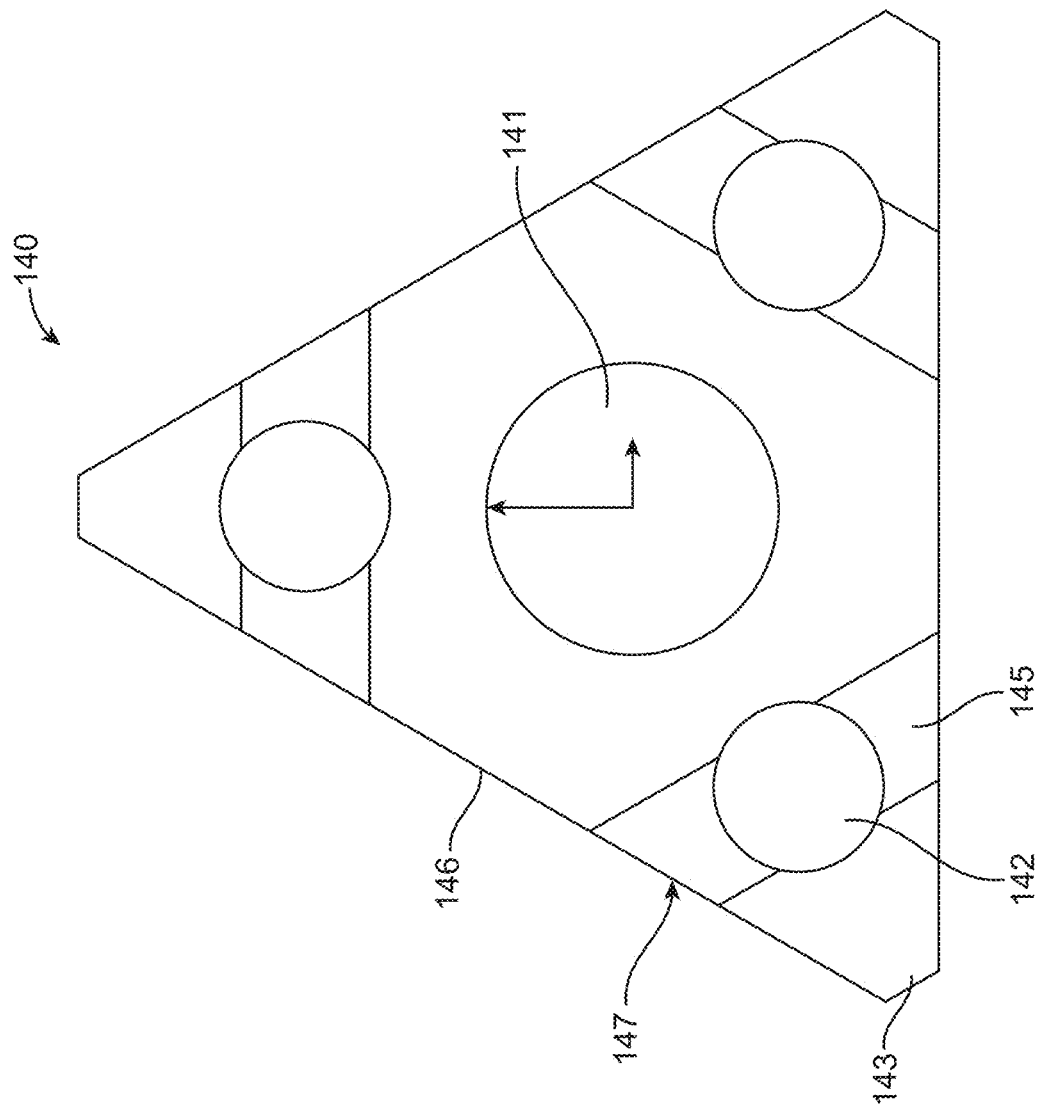

FIGS. 1N-P illustrate another embodiment of an implant structure 140 having a central lumen 141 and a plurality of peripheral lumens 142 surrounding the central lumen 141. The peripheral lumens 142 can be oriented longitudinally and can be located between the central lumen 141 and each apex 143. As illustrated, the implant structure 140 is triangular and has three apexes 143 and three peripheral lumens 142 that surround the central lumen 141. In some embodiments, both the central lumen 141 and the peripheral lumens 142 can extend throughout the longitudinal length of the implant structure 140. In other embodiments, the peripheral lumens 142 do not extend throughout the length of the implant structure 140, and instead, the peripheral lumens 142 terminate prior to the distal end 144 of the implant structure 140. In addition, a plurality of side holes 145 can be included in the implant structure 140. Each peripheral lumen 142 can be intersected by a plurality of side holes 145, where each side hole 145 extends between two faces 146 of the implant structure with a side hole opening 147 on each of the two faces 146. The side holes 145 can extend transversely through the implant structure 140 at an angle of about 60 degrees from the surfaces of the faces 146. In some embodiments, each apex 143 can be beveled or rounded. In some embodiments, the distal end 144 of the implant structure 140 can be tapered to facilitate implantation into the bone. In some embodiments, the implant structure 140 illustrated in FIGS. 1N-P has a relative bending strength of about 0.63 and a relative shear strength of about 0.66. In some embodiments, to load the implant structure 140 with bone graft materials, the bone graft material is injected into the peripheral lumens 142, where the bone graft material fills up the peripheral lumens and exits the side holes 145. Injection of the bone graft material can take place before, during, or after implantation. In some embodiments where the peripheral lumens 142 extend completely through the implant structure 140, the distal ends of the peripheral lumens 142 can be blocked or plugged before injection of the bone graft material.

In some embodiments, the peripheral lumens 142 have a diameter (D3) of about 0.2 times the width (W7) of the faces 146 of the implant structure. In some embodiments, the peripheral lumens 142 have a diameter greater than or less than about 0.2 times the width of the faces 146 of the implant structure. In some embodiments, the peripheral lumens 142 can have a smaller diameter than the central lumen 141. In other embodiments, the peripheral lumens 142 can have an equal or larger diameter than the central lumen 141. In some embodiments, the side holes 145 have a diameter (D4) equal or substantially equal to the diameter of the peripheral lumens 142. In other embodiments, the side holes 145 have a diameter less than or greater than the diameters of the peripheral lumens 142. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1Q:
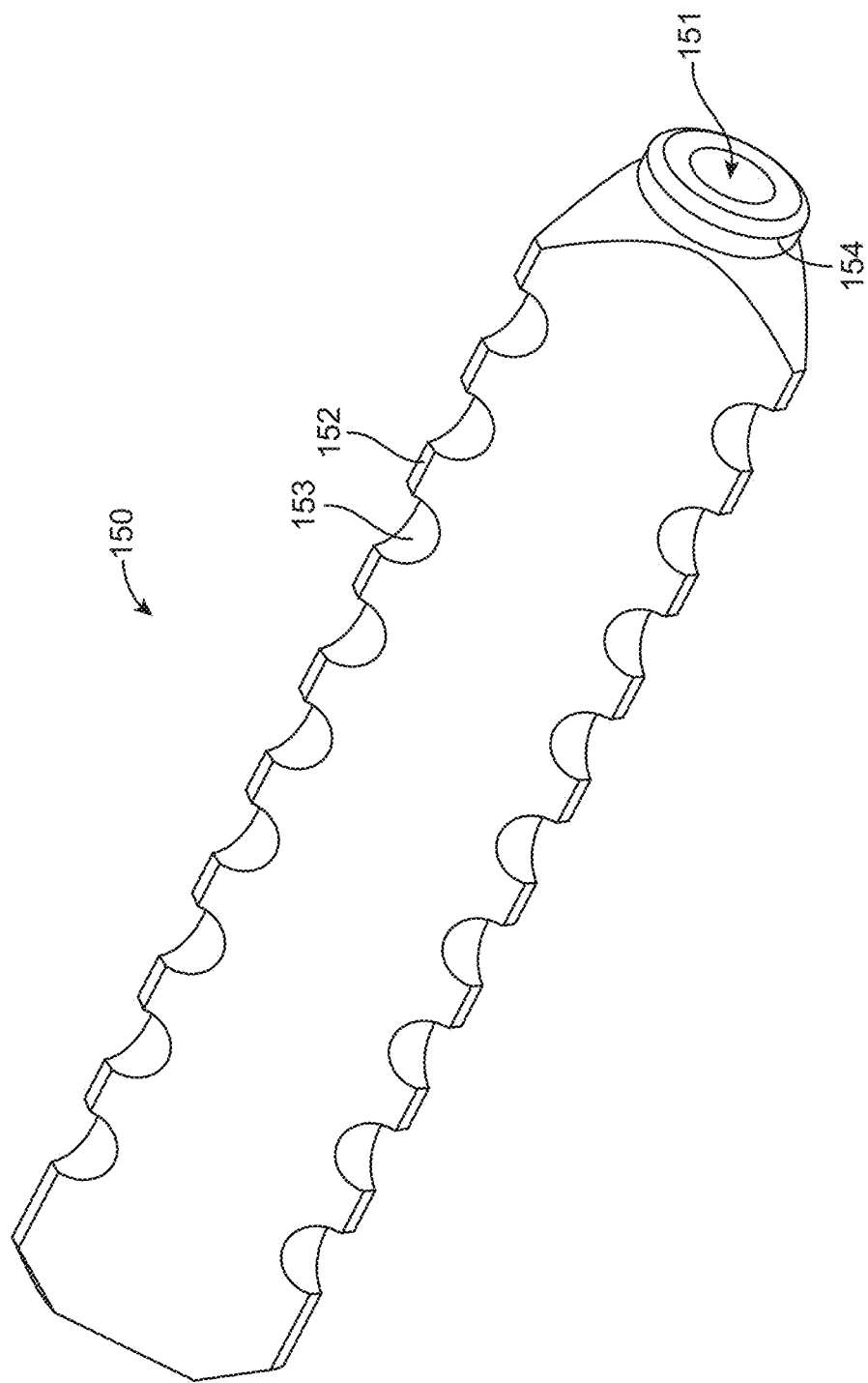
Figure 1R:
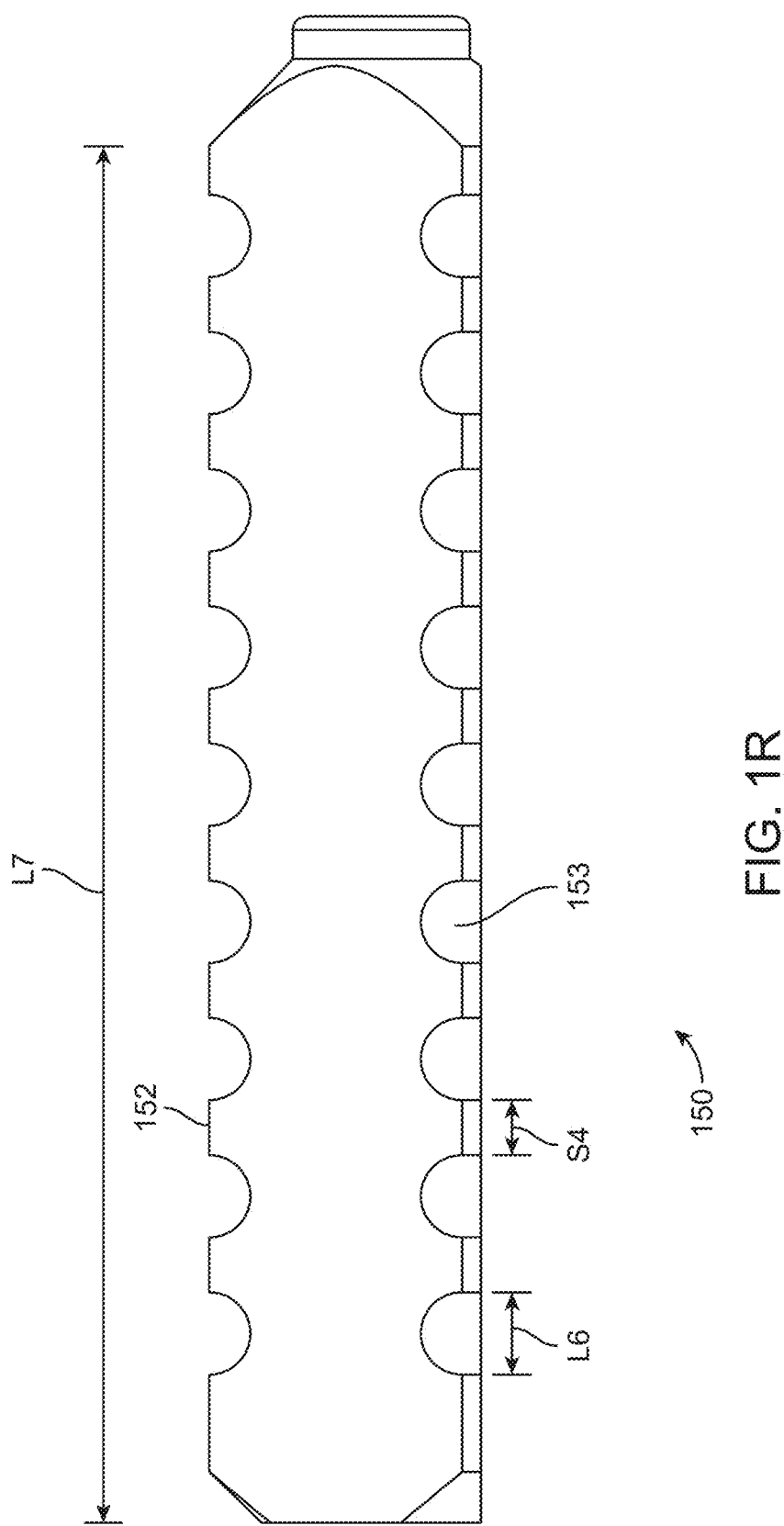
Figure 1S:
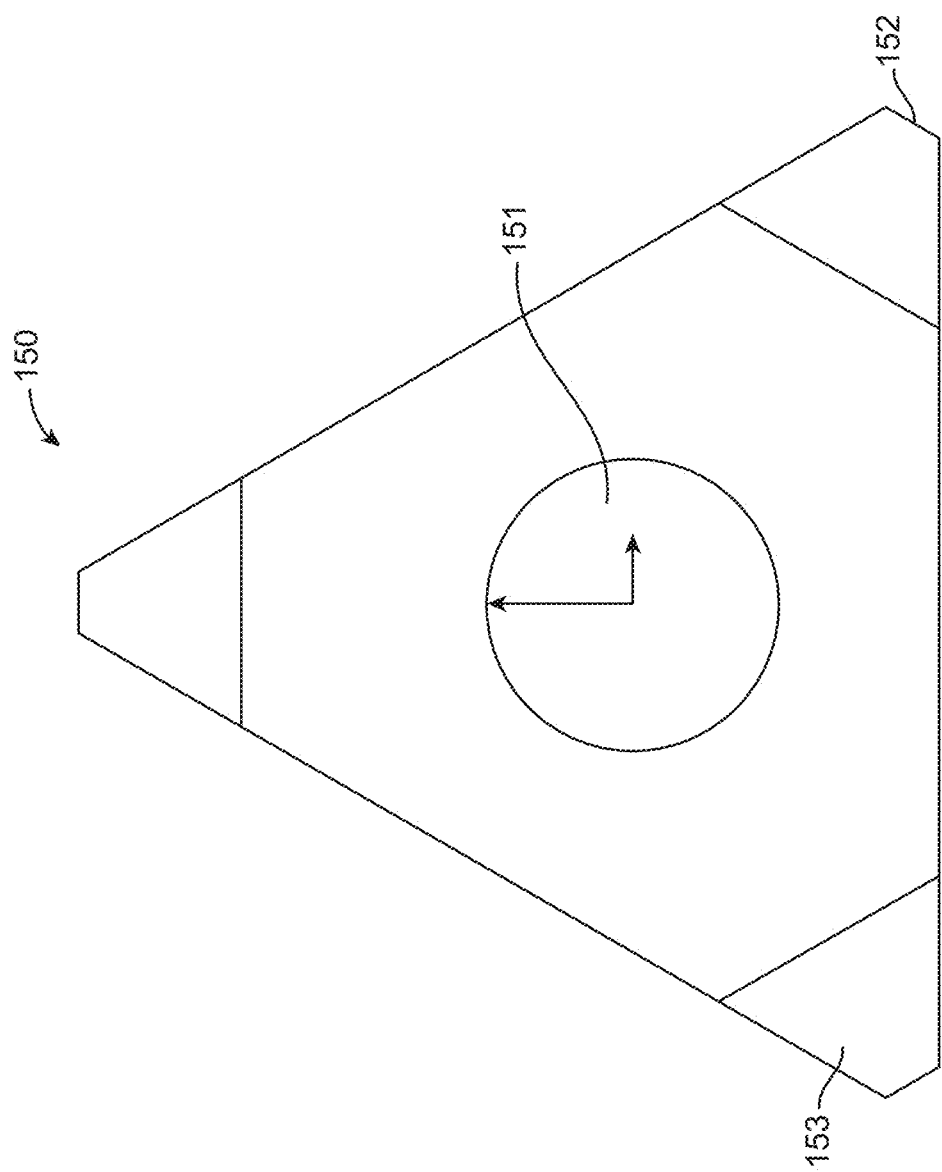

FIGS. 1Q-S illustrate another embodiment of an implant structure 150 having a central lumen 151. Each apex 152 can be beveled or rounded and can have a plurality of pockets or cavities 153 located at discrete points along the length of the apex 152. These pockets 153 extend from the apex 152 and towards the central lumen 151, but do not reach the central lumen 151. In some embodiments, the pockets 153 have a curved cutout shape, which can correspond in shape to a portion of a cylinder. In some embodiments, the distal end 154 of the implant structure 140 can be tapered to facilitate implantation into the bone. In some embodiments, the implant structure 150 illustrated in FIGS. 1Q-S has a relative bending strength of about 0.89 and a relative shear strength of about 0.86. In some embodiments, to load the implant structure 150 with bone graft materials, the bone graft material is applied externally to the implant structure 150 either before or during implantation. In addition to receiving the bone graft materials, the pockets 153 also function to eliminate or reduce a corner haloing effect.

In some embodiments, the pockets 153 can have a length (L6) or diameter of about 0.06 of the length (L7) of the apex 152. In some embodiments, the pockets 153 can have a length or diameter greater than or less than about 0.06 of the length of the apex 152. In some embodiments, the pockets 153 can be separated (S4) from adjacent pockets 153 by about ⅔ of the pocket length or diameter. In some embodiments, the pockets 153 can be separated from adjacent pockets 153 by greater than or less than about ⅔ of the hole diameter. In some embodiments, the relative bending strength can be at least about 0.5, 0.6, 0.7, 0.8 or 0.9. In some embodiments, the relative bending strength can be between about 0.5 to 0.95. In some embodiments, the relative shear strength can be at least about 0.5, 0.6, 0.7, 0.8 or 0.9. In some embodiments, the relative shear strength can be between about 0.5 to 0.95.

Figure 1T:
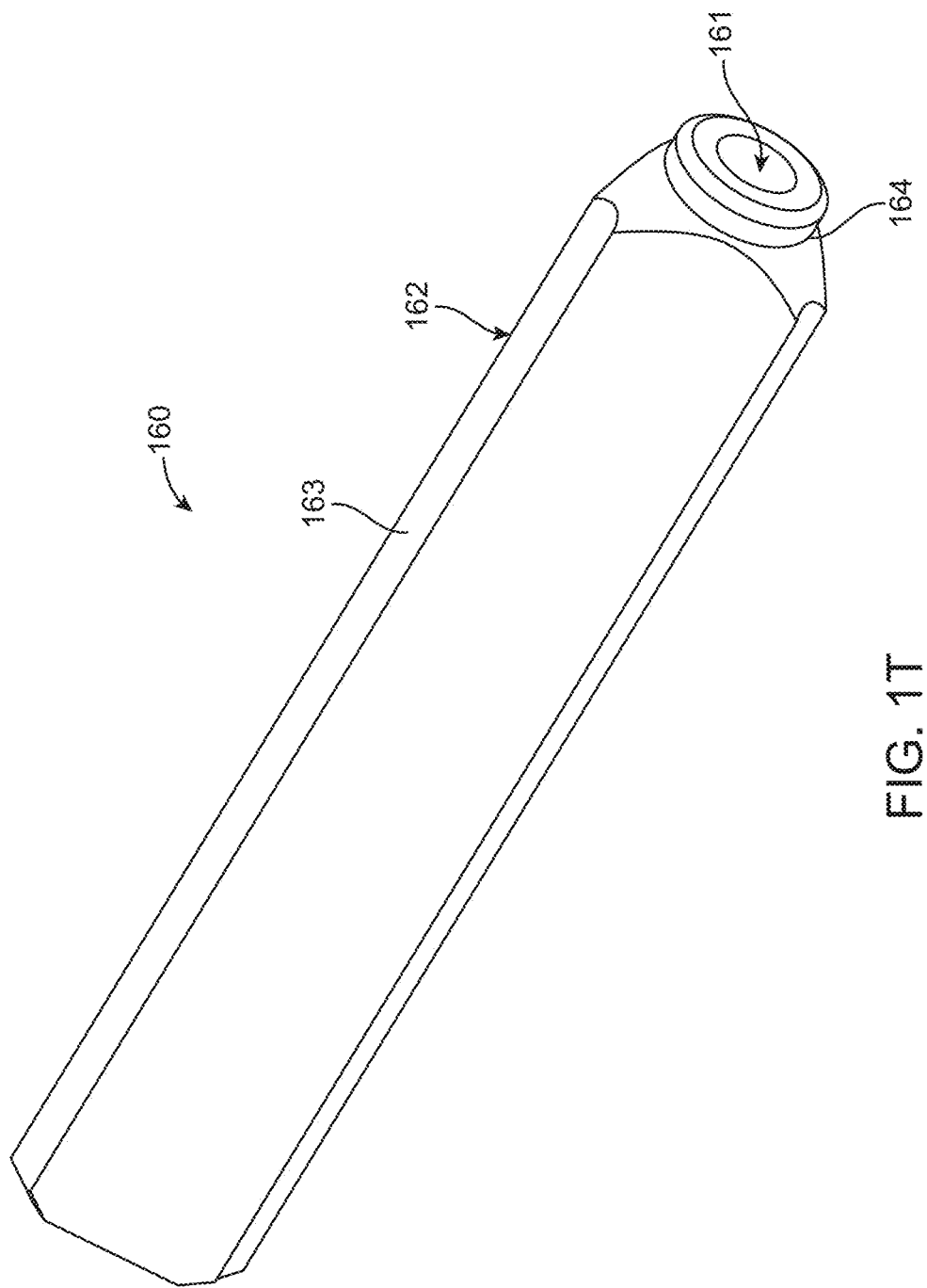
Figure 1U:
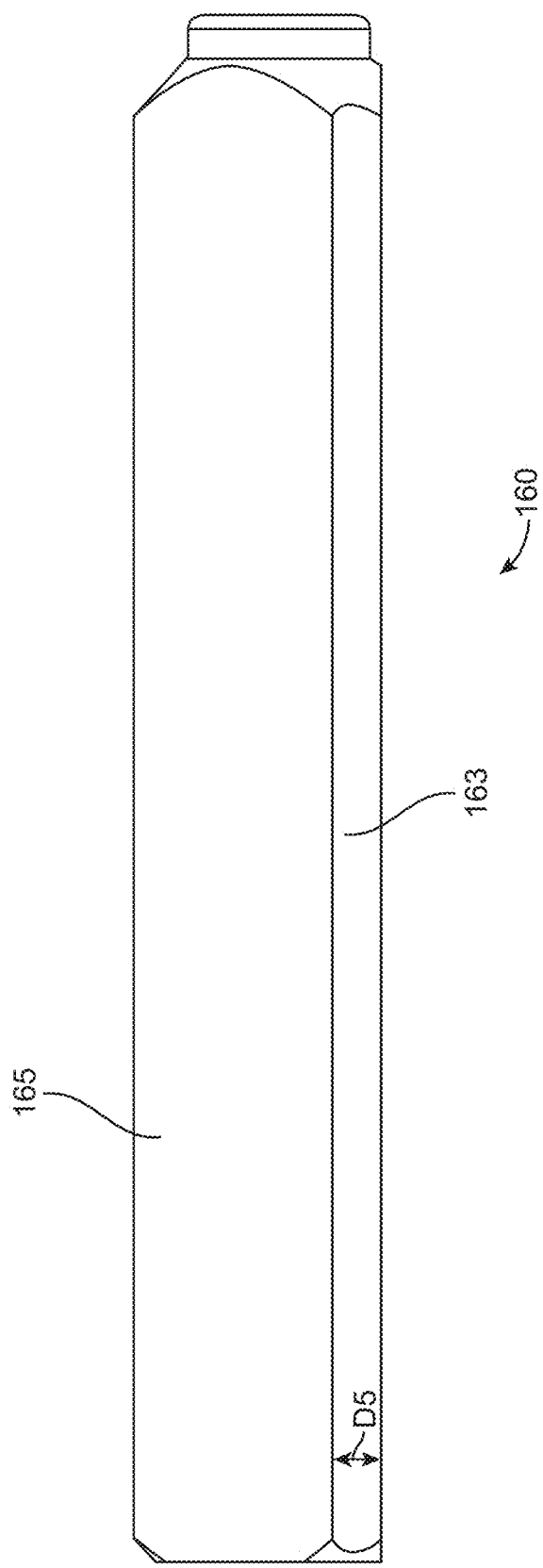
Figure 1V:
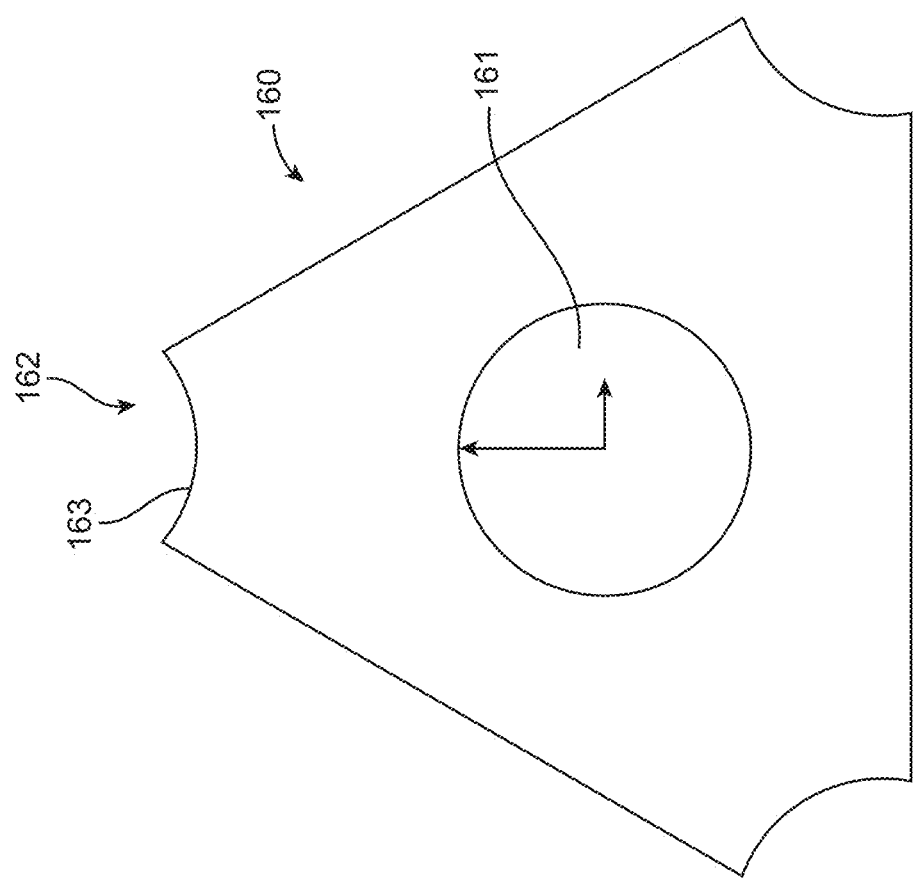

FIGS. 1T-V illustrate another embodiment of an implant structure 160 having a central lumen 161. Each apex 162 has a groove 163 that extends along the length of the apex 162. In some embodiments, the distal end 164 of the implant structure 160 can be tapered to facilitate implantation into the bone. In some embodiments, the implant structure 160 illustrated in FIGS. 1T-V has a relative bending strength of about 0.87 and a relative shear strength of about 0.88. In some embodiments, to load the implant structure 160 with bone graft materials, the bone graft material is applied externally to the implant structure 160 either before or during implantation. In addition to receiving the bone graft materials, the grooves 163 also function to eliminate or reduce a corner haloing effect.

In some embodiments, the grooves 163 can be circular shaped cutouts running along the apex 162 having a diameter (D5) of about 0.25 of the width of the face 165 and an arc length of about 0.28 of the width of the face 165. In some embodiments, the grooves 163 can have a diameter of greater or less than about 0.25 of the width of the face 165. In some embodiments, the grooves 163 can have an arc length of greater than or less than about 0.28 of the width of the face 165.

In one embodiment of a lateral approach (see FIGS. 5, 6, and 7A/B), one or more implant structures 20 are introduced laterally through the ilium, the SI-Joint, and into the sacrum. This path and resulting placement of the implant structures 20 are best shown in FIGS. 6 and 7A/B. In the illustrated embodiment, three implant structures 20 are placed in this manner. Also in the illustrated embodiment, the implant structures 20 are rectilinear in cross section and triangular in this case, but it should be appreciated that implant structures 20 of other cross sections can be used. In addition, any of the implant structures disclosed above can be used in the implantation procedures herein.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI Joint injection.

Figure 2A:
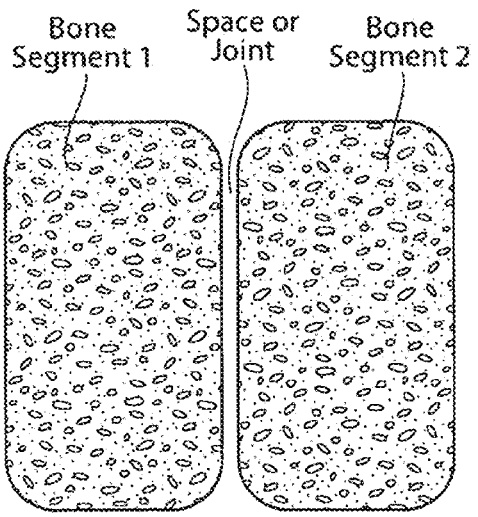
Figure 2B:
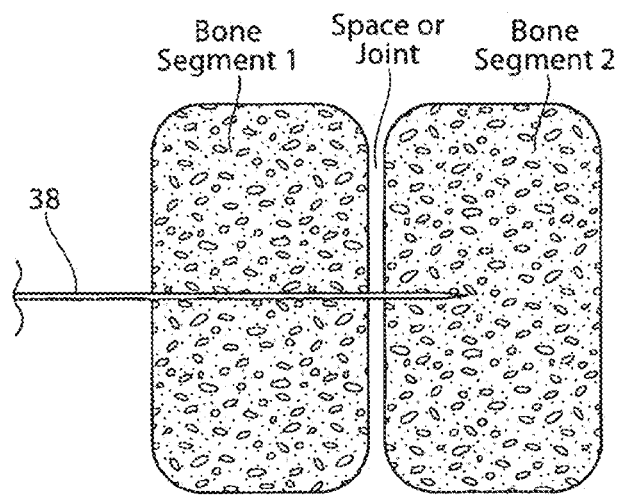

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate at a shallow angle anterior (e.g., 15 to 20 degrees off horizontal, as FIG. 7B shows). In a lateral view, the guide pin 38 should be posterior to the sacrum anterior wall. In the inlet view, the guide pin 38 should not violate the sacral foramina. This corresponds generally to the sequence shown diagrammatically in FIGS. 2A and 2B. A soft tissue protector (not shown) is desirably slipped over the guide pin 38 and firmly against the ilium before removing the guide pin sleeve (not shown).

Figure 2C:
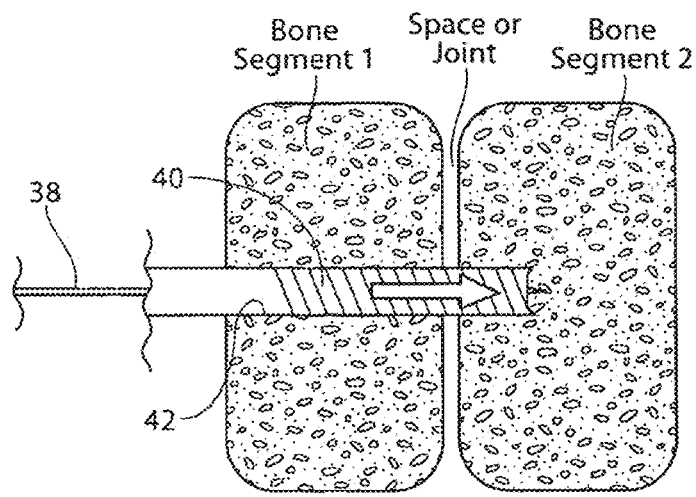

Over the guide pin 38 (and through the soft tissue protector), the pilot bore 42 is drilled in the manner previously described, as is diagrammatically shown in FIG. 2C. The pilot bore 42 extends through the ilium, through the SI-Joint, and into the sacrum. The drill bit 40 is then removed.

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 2D. The triangular profile of the broached bore 48 is also shown in FIG. 5.

Figure 2E:
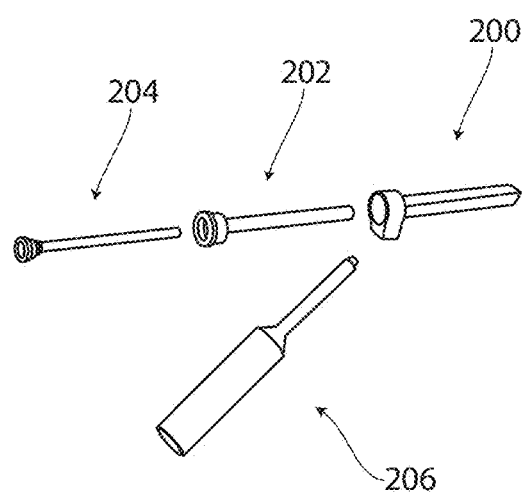
FIGS. 2E and 2F illustrate the assembly of a soft tissue protector system for placement over a guide wire.
Figure 2F:
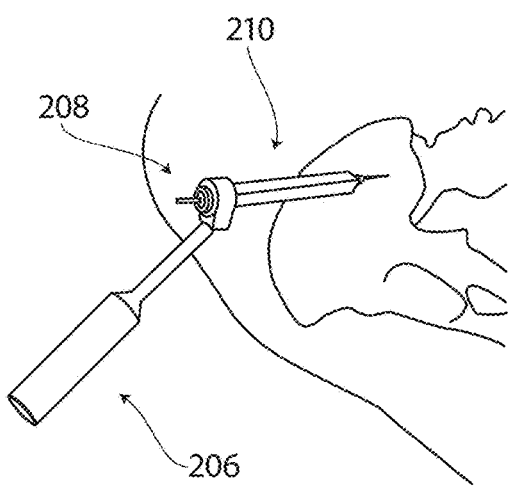

FIGS. 2E and 2F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 as disclosed herein can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 5:
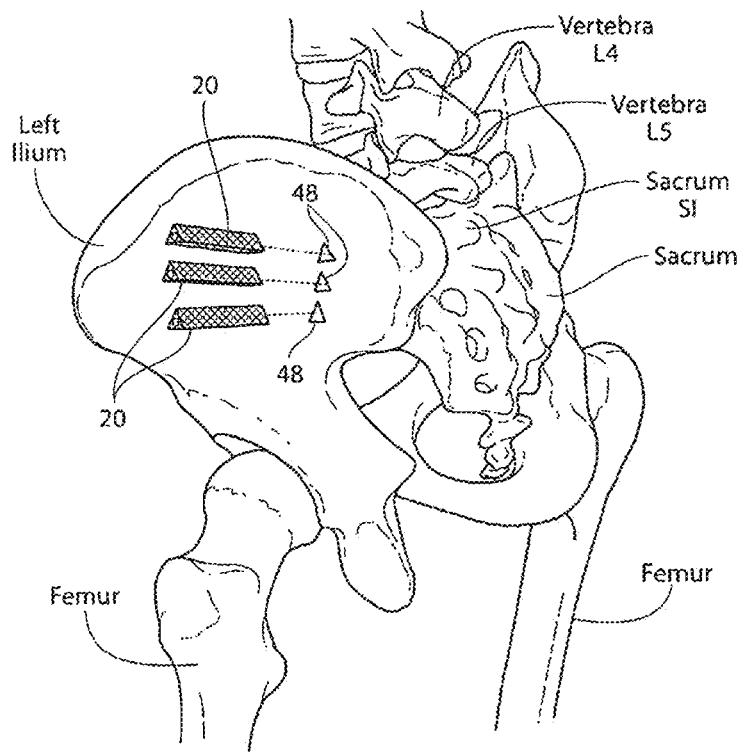
Figure 6:
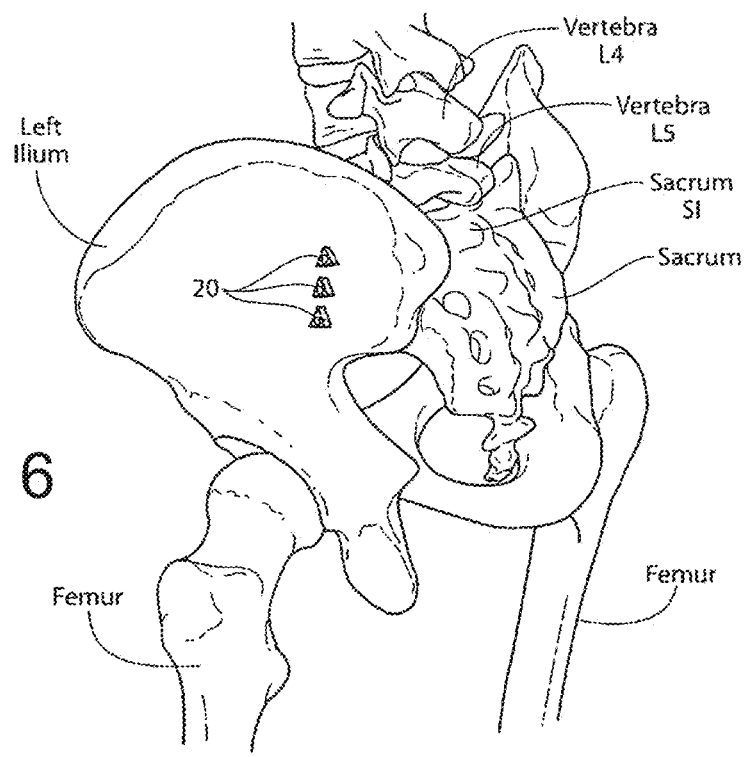
Figure 7A:
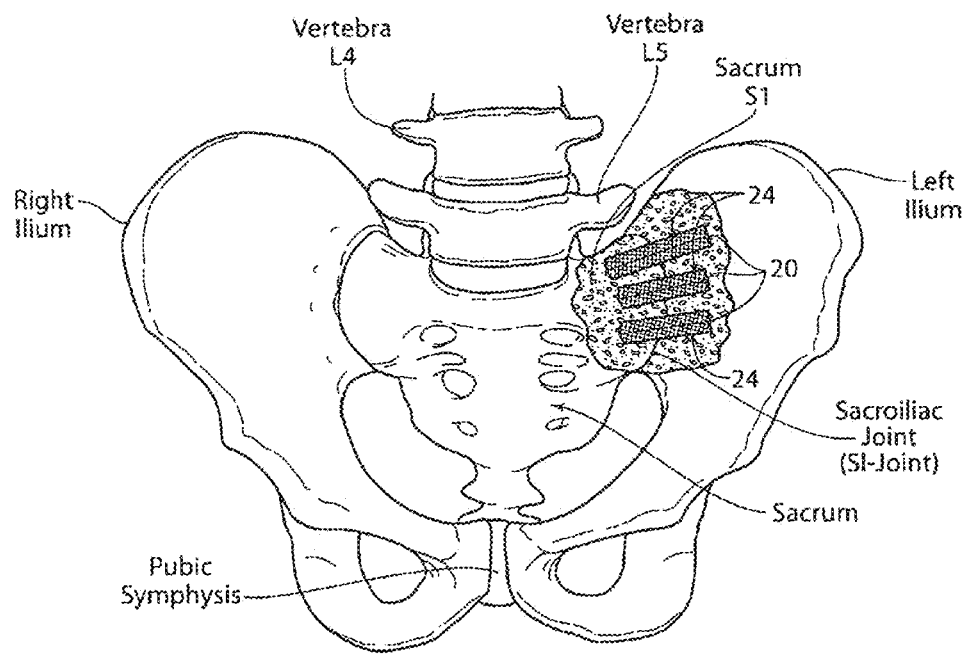
Figure 7B:
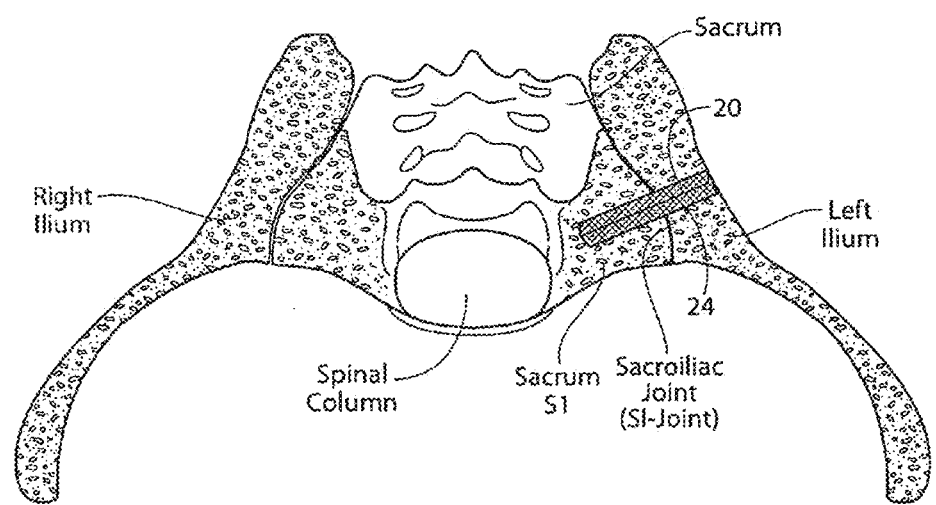

As shown in FIGS. 5 and 6, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 7A and 7B). The guide pin 38 and soft tissue protector are withdrawn, leaving the implant structure 20 residing in the broached passageway, flush with the lateral wall of the ilium (see FIGS. 7A and 7B). In the illustrated embodiment, two additional implant structures 20 are implanted in this manner, as FIG. 6 best shows. In other embodiments, the proximal ends of the implant structures 20 are left proud of the lateral wall of the ilium, such that they extend 1, 2, 3 or 4 mm outside of the ilium. This ensures that the implants 1020 engage the hard cortical portion of the ilium rather than just the softer cancellous portion, through which they might migrate if there was no structural support from hard cortical bone. The hard cortical bone can also bear the loads or forces typically exerted on the bone by the implant 1020.

The implant structures 20 are sized according to the local anatomy. For the SI-Joint, representative implant structures 20 can range in size, depending upon the local anatomy, from about 35 mm to about 70 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Application No. 61/609,043, titled "TISSUE DILATOR AND PROTECTER" and filed Mar. 9, 2012, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium alloy provide immediate post-op SI Joint stability. A bony in-growth region 24 comprising a porous plasma spray coating with irregular surfaces supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

Figure 8A:
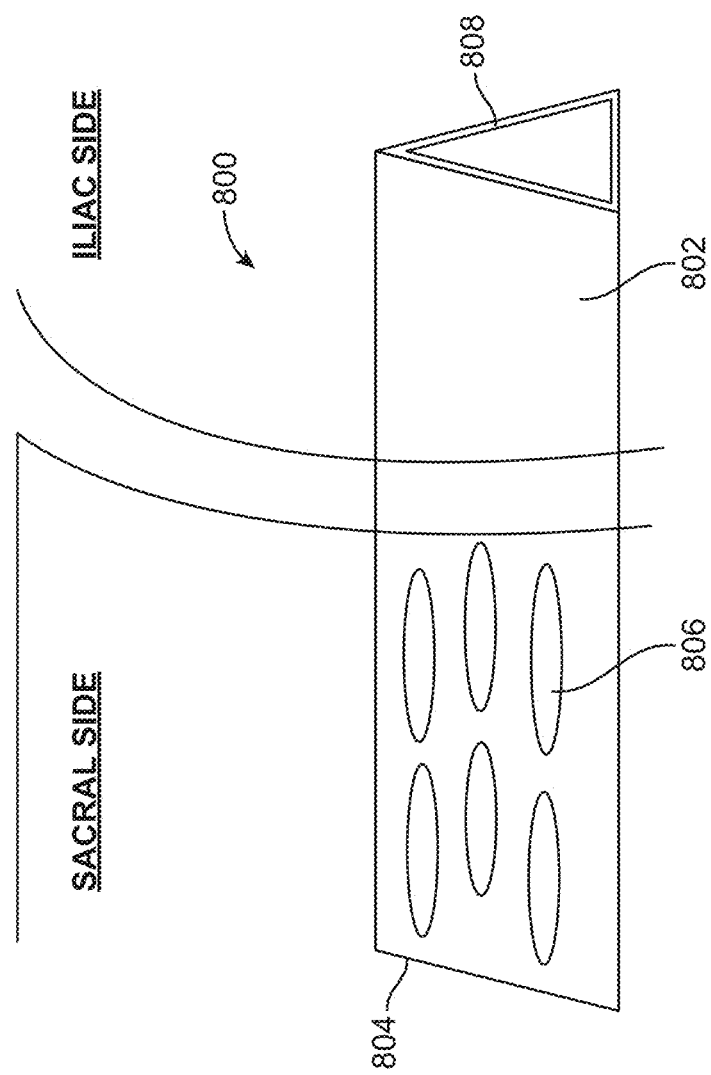
Figure 8C:
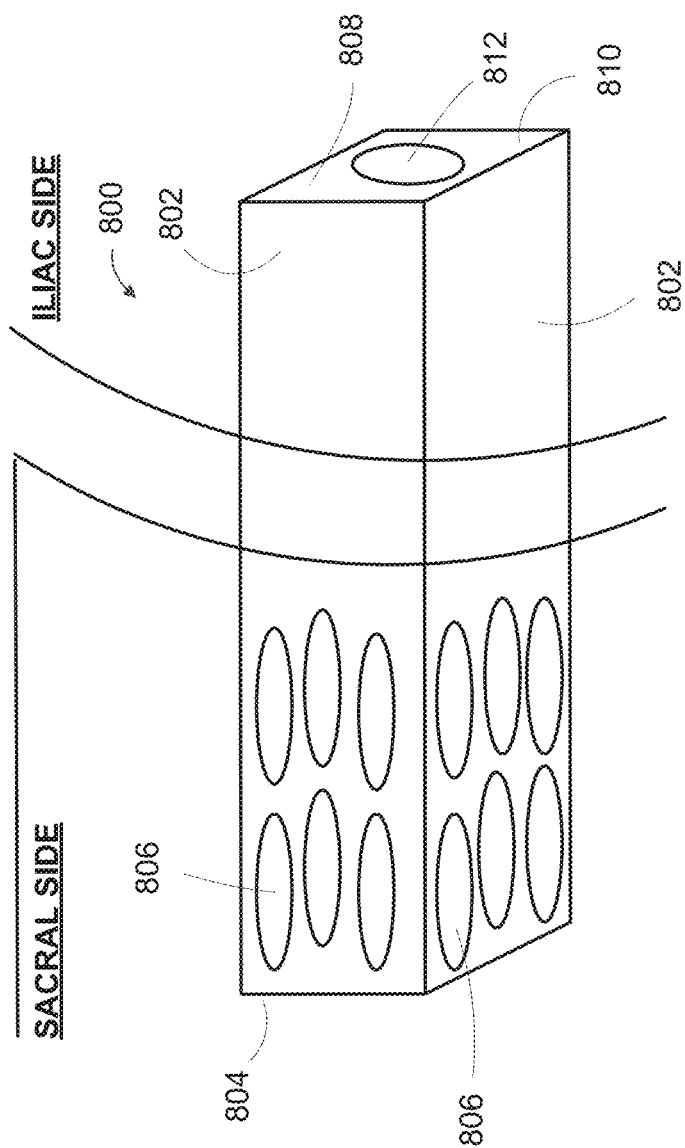

In some embodiments, as illustrated in FIGS. 8A and 8B, the implant structure 800 can have a rectilinear cross-sectional profile formed from a plurality of walls 802 having a thickness of approximately 2 to 3 mm, or 1 to 5 mm, or less than approximately 5, 4, 3, or 2 mm. In some embodiments, the rectilinear cross-sectional profile can be triangular, square or rectangular. In some embodiments, the implant structure 800 can have a substantially rectilinear cross-sectional profile formed by a plurality of apices that are joined together by a plurality of walls. The thin walled implant structure 800 can be advanced through the bone with little to no bony preparation. For example, in some embodiments, the implant structure 800 can be driven into the bone without first forming a bore that is shaped like the implant structure 800. In some embodiments, the distal end 804 of the implant structure 800 can be sharpened and/or have cutting edges like a chisel to facilitate the cutting of bone as the implant structure 800 is advanced. In some embodiments, an osteotome can be used to cut the bone before the implant structure 800 is inserted into the bone. For example, an osteotome as described in U.S. Provisional Application 61/800,966, titled "SYSTEMS AND METHODS FOR REMOVING AN IMPLANT" and filed on Mar. 15, 2013, which is herein incorporated by reference in its entirety for all purposes, can be adapted to pre-cut the bone to facilitate insertion of the implant structure 800 without forming a complete bore. In some embodiments, a bore can be formed as described above, and the implant structure 800 can then be inserted into the bore.

Figure 9A:
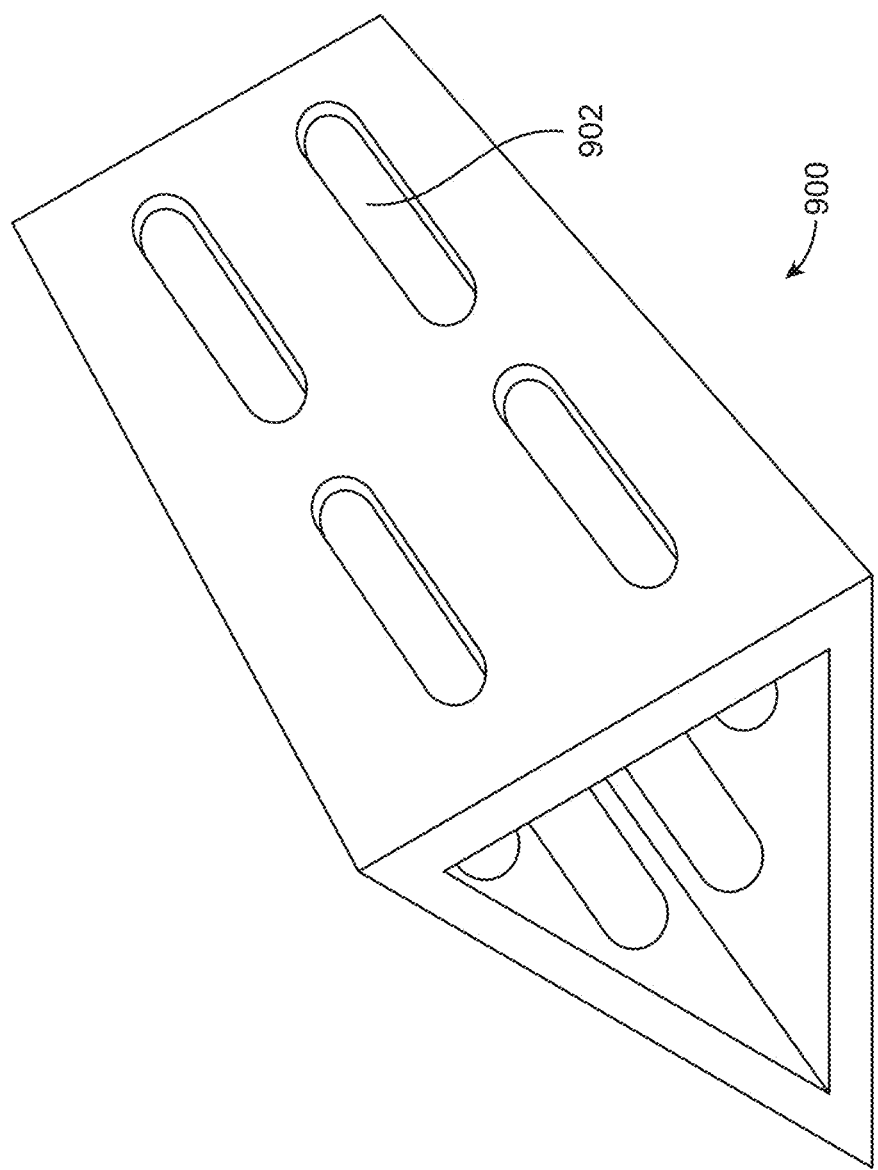
FIGS. 9A and 9B illustrate yet another embodiment of an implant structure with fenestrations.
Figure 9B:
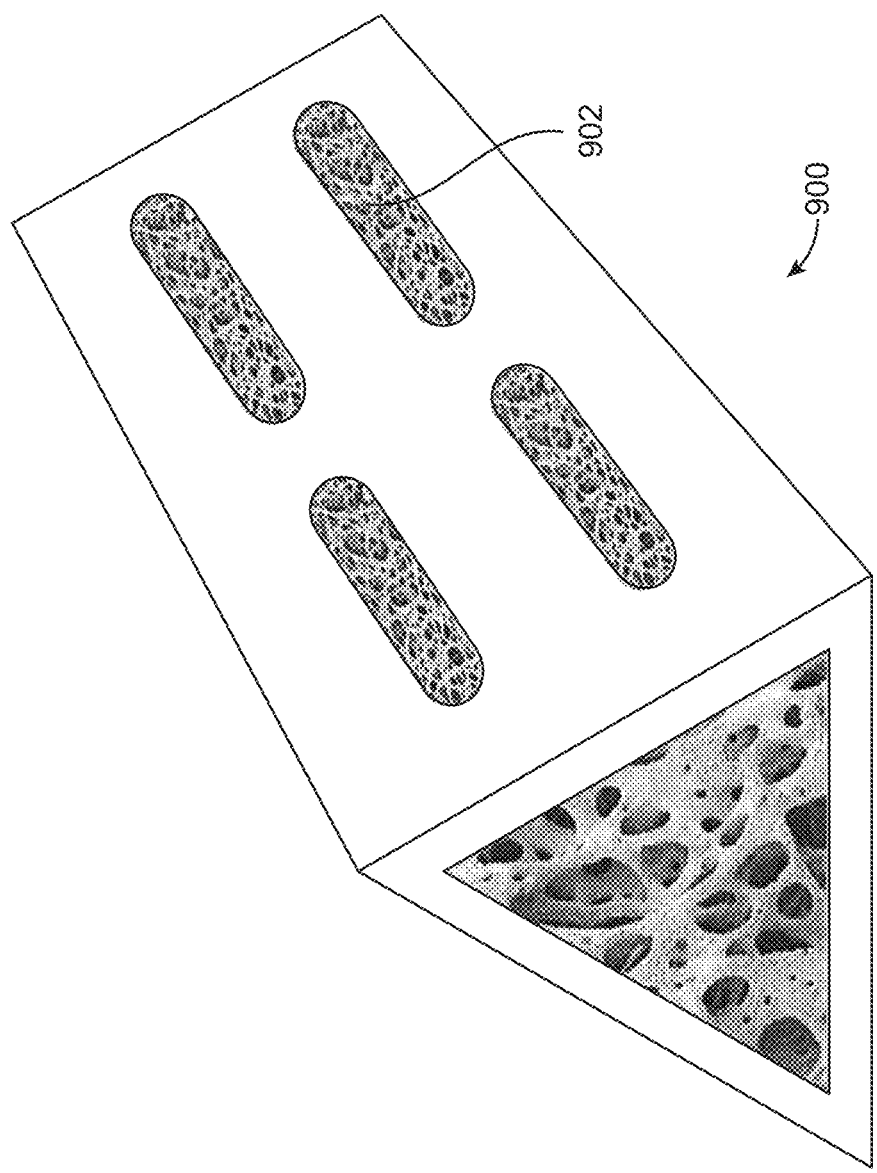

In some embodiments, as illustrated in FIGS. 8A and 8B, the distal portion of the plurality of walls 802 forming the implant structure 800 can have fenestrations 806. For example, the distal portion of the implant structure 800 that is configured to be embedded in the sacrum or second bone segment can be fenestrated, while the proximal portion of the implant structure 800 that is configured to be embedded in the ilium or first bone segment can be free from fenestrations. In other embodiments, the proximal portion of the implant structure 800 can be fenestrated while the distal portion of the implant structure 800 can be free from fenestration. In other embodiments, as illustrated in FIGS. 9A and 9B and the other embodiments described herein, the fenestrations can be distributed across the entire face of each wall or side of the implant structure. In some embodiments, the concentration or number of fenestrations can be higher in one portion of the implant structure than the other.

In some embodiments, as illustrated in FIGS. 8A and 8B, the fenestrations 806 can be oval or circular shaped or curvilinear, such that the fenestrations 806 do not have corners. In some embodiments, the fenestrations 806 can be staggered, arranged randomly, or otherwise distributed in a non-aligned pattern across each wall 802. For example, in some embodiments, each longitudinal row of fenestrations can be staggered or offset from adjacent longitudinal rows of fenestrations. In some embodiments, the fenestrations can alternatively or additionally be staggered along the longitudinal axis of the implant structure 800. This non-aligned arrangement of fenestrations can provide the implant structure with improved structural strength.

In some embodiments, the implant structure 800 can be sized as any other implant structure described herein. In some embodiments, the implant structure 800 can be sized so that the implant structure 800 has walls that inscribe a circle with a diameter of about 8 mm, or between about 4 and 12 mm, as illustrated in FIG. 8B. In some embodiments, the implant structure 800 can be sized so that the wall inscribe a circle with a diameter equal to or about equal to the diameter of a guide pin. In some embodiments, the implant structure 800 can have a proximal end 808 having a cap 810 with a circular opening 812 that allows passage of a guide pin.

In some embodiments, as illustrated in FIGS. 9A and 9B, the implant structure 900 can be similar to the embodiment described in FIGS. 8A and 8B except that the fenestrations 902 are evenly distributed across the faces of the implant structure. FIG. 9B illustrates bone growing within and/or through the fenestrations 902 and lumen of the implant structure 900. In some embodiments, the bone illustrated within the lumen of the implant structure 900 may be native bone that remains after the implant structure 900 is advanced into the bone, i.e. a self-grafting implant. In some embodiments, the lumen of the implant structure 900 illustrated in FIGS. 9A and 9B, as well as the other implant structures described herein, can be filled with bone material and/or a biologic aid such as morselized bone, allograft bone, autograft bone, hydroxyapatite, bone morphogenetic protein and the like to promote bony ingrowth within the implant structure 900. This can be appropriate when the implant structure 900 is inserted into a bore such that after implantation, the lumen of the implant structure 900 is empty or substantially empty and can be filled with bone growth promoting materials. In addition, as described above, the interior surface and/or the outer surface of the implant structure can be roughened and/or coated, using a plasma coating process for example, to provide a porous or roughened surface.

The terms "about" and "approximately" and the like can mean within 10, 20, or 30% of the stated value or range.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiments whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of stabilizing a sacroiliac (SI) joint, comprising:
    applying an axially directed, non-rotational, force to advance an SI joint implant laterally through an ilium, across an SI joint, and into a sacrum,
        the implant comprising an elongate body having a longitudinal axis, a distal end, a proximal end, a triangular cross sectional profile with three sides transverse to the longitudinal axis and extending from a proximal half of the elongate body into a distal half of the elongate body, each of the three sides including a fenestration region having therein a plurality of fenestrations, and
        wherein the elongate body has a bending strength or a shear strength of at least 0.5 relative to a reference elongate body with identical dimensions and material composition but without any fenestrations;
    positioning the distal end of the elongate body in the sacrum, the proximal end of the elongate body in the ilium, and the fenestation region across the SI joint to facilitate at least one of bony in-growth, on-growth, or through-growth with the plurality of fenestrations.

2. The method of claim 1, wherein the elongate body includes an axially-extending central lumen disposed about the longitudinal axis, and wherein the plurality of fenestrations does not extend to the central lumen.

3. The method of claim 1, wherein each of the plurality of fenestrations extends inwardly at an angle that is substantially perpendicular or normal to a related corresponding side of the three sides in which each of the plurality of fenestrations is disposed.

4. The method of claim 1, wherein each of the plurality of fenestrations extends inwardly at an angle that is not substantially perpendicular or normal to a related corresponding side of the three sides in which each of the plurality of fenestrations is disposed.

5. The method of claim 1, wherein each of the plurality of fenestrations extends from a first side to an adjacent side.

6. The method of claim 1, wherein each of the plurality of fenestrations has a curvilinear configuration.

7. The method of claim 1, wherein each of the plurality of fenestrations, in a side view, has an oval configuration.

8. The method of claim 1, wherein at least some of the plurality of fenestrations on each side are randomly arranged on a related corresponding side of the three sides in which each of the at least some of the plurality of fenestrations is disposed.

9. The method of claim 1, wherein at least some of the plurality of fenestrations on each side are arranged in one or more rows along a length of a related corresponding side of the three sides in which each of the at least some of the plurality of fenestrations is disposed.

10. The method of claim 1, wherein the distal end of the elongate body comprises a tapered configuration to facilitate implantation into the bone.

11. The method of claim 1, wherein the elongate body includes an axially-extending central lumen disposed about the longitudinal axis, and wherein the plurality of fenestrations extend to the central lumen.

* * * * *